US007501426B2

(12) United States Patent
Himmelsbach et al.

(10) Patent No.: US 7,501,426 B2
(45) Date of Patent: Mar. 10, 2009

(54) 8-[3-AMINO-PIPERIDIN-1-YL]-XANTHINES, THEIR PREPARATION AND THEIR USE AS PHARMACEUTICAL COMPOSITIONS

(75) Inventors: Frank Himmelsbach, Mittelbiberach (DE); Elke Langkopf, Warthausen (DE); Matthias Eckhardt, Biberach (DE); Mohammad Tadayyon, Ulm (DE); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 290 days.

(21) Appl. No.: 11/060,703

(22) Filed: Feb. 17, 2005

(65) Prior Publication Data

US 2005/0234108 A1 Oct. 20, 2005

Related U.S. Application Data

(60) Provisional application No. 60/551,108, filed on Mar. 8, 2004, provisional application No. 60/562,573, filed on Apr. 15, 2004.

(30) Foreign Application Priority Data

| | | |
|---|---|---|
| Feb. 18, 2004 | (DE) | 10 2004 008 112 |
| Mar. 17, 2004 | (DE) | 10 2004 012 921 |
| Jul. 3, 2004 | (DE) | 10 2004 032 263 |

(51) Int. Cl.

| | |
|---|---|
| ***C07D 473/06*** | (2006.01) |
| ***A61K 31/522*** | (2006.01) |
| ***A61P 3/10*** | (2006.01) |
| *A61P 19/02* | (2006.01) |
| *A61P 3/04* | (2006.01) |

(52) U.S. Cl. ............ 514/263.21; 514/263.22; 514/263.23; 514/263.34; 544/269; 544/270; 544/272

(58) Field of Classification Search ............ 514/263.2, 514/263.21, 263.22, 263.23, 263.24, 263.34, 514/263.36; 544/268, 269, 270, 272
See application file for complete search history.

(56) References Cited

U.S. PATENT DOCUMENTS

| | | | | |
|---|---|---|---|---|
| 2,928,833 | A | 3/1960 | Leake et al. | |
| 4,005,208 | A | 1/1977 | Bender | |
| 4,599,338 | A | 7/1986 | Regnier et al. | |
| 5,041,448 | A | 8/1991 | Janssens | |
| 5,051,517 | A | 9/1991 | Findeisen | |
| 5,223,499 | A | 6/1993 | Greenlee et al. | |
| 5,234,897 | A | 8/1993 | Findeisen et al. | |
| 5,258,380 | A | 11/1993 | Janssens | |
| 5,266,555 | A | 11/1993 | Findeisen et al. | |
| 5,389,642 | A | 2/1995 | Dorsch | |
| 5,470,579 | A | 11/1995 | Bonte et al. | |
| 5,719,279 | A | 2/1998 | Kuefner-Muhl et al. | |
| 5,753,635 | A | 5/1998 | Buckman et al. | |
| 6,303,661 | B1 | 10/2001 | Demuth | |
| 6,342,601 | B1 | 1/2002 | Bantick | |
| 6,548,481 | B1 | 4/2003 | Demuth et al. | |
| 6,579,868 | B1 | 6/2003 | Asano | |
| 6,784,195 | B2 | 8/2004 | Hale et al. | |
| 6,821,978 | B2 | 11/2004 | Chackalamannil | |
| 6,869,947 | B2 | 3/2005 | Kanstrup | |
| 7,060,722 | B2 | 6/2006 | Kitajima | |
| 7,074,794 | B2 | 7/2006 | Kitajima | |
| 7,074,798 | B2 | 7/2006 | Yoshikawa | |
| 7,074,923 | B2 | 7/2006 | Dahanukar | |
| 7,109,192 | B2 | 9/2006 | Hauel | |
| 7,179,809 | B2 | 2/2007 | Eckhardt | |
| 7,183,280 | B2 * | 2/2007 | Himmelsbach et al. | 514/248 |
| 7,192,952 | B2 | 3/2007 | Kanstrup | |
| 7,217,711 | B2 | 5/2007 | Eckhardt | |
| 7,235,538 | B2 | 6/2007 | Kanstrup et al. | |
| 2002/0161001 | A1 | 10/2002 | Kanstrup | |
| 2002/0169174 | A1 | 11/2002 | Chackalamannil | |
| 2002/0198205 | A1 | 12/2002 | Himmelsbach | |
| 2003/0105077 | A1 | 6/2003 | Kanstrup et al. | |
| 2003/0199528 | A1 | 10/2003 | Kanstrup | |
| 2003/0232987 | A1 | 12/2003 | Dahanukar et al. | |
| 2003/0236272 | A1 | 12/2003 | Carr | |
| 2004/0034014 | A1 | 2/2004 | Kanstrup et al. | |
| 2004/0077645 | A1 | 4/2004 | Himmelsbach et al. | |
| 2004/0082570 | A1 | 4/2004 | Yoshikawa | |

(Continued)

FOREIGN PATENT DOCUMENTS

CA 2136288 A1 5/1995

(Continued)

OTHER PUBLICATIONS

Busso et al., American Journal of Pathology 166:433-442 (2005).*

(Continued)

*Primary Examiner*—Mark L Berch
(74) *Attorney, Agent, or Firm*—Michael P. Morris; Mary-Ellen M. Devlin; David L. Kershner

(57) ABSTRACT

Disclosed are substituted xanthines of the formula (I)

wherein R is defined as in claim 1, the tautomers, the stereoisomers, the mixtures thereof and the salts thereof, which have valuable pharmacological properties, particularly an inhibiting effect on the activity of the enzyme dipeptidylpeptidase-IV (DPP-IV).

20 Claims, No Drawings

U.S. PATENT DOCUMENTS

| | | | | |
|---|---|---|---|---|
| 2004/0087587 | A1 | 5/2004 | Himmelsbach et al. | |
| 2004/0097510 | A1 | 5/2004 | Himmelsbach et al. | |
| 2004/0116328 | A1 | 6/2004 | Yoshikawa et al. | |
| 2004/0122228 | A1 | 6/2004 | Maier | |
| 2004/0138214 | A1* | 7/2004 | Himmelsbach et al. | 514/230.5 |
| 2004/0138215 | A1 | 7/2004 | Eckhardt | |
| 2004/0166125 | A1 | 8/2004 | Himmelsbach | |
| 2005/0020574 | A1 | 1/2005 | Hauel et al. | |
| 2005/0026921 | A1 | 2/2005 | Eckhardt | |
| 2005/0130985 | A1 | 6/2005 | Himmelsbach | |
| 2005/0171093 | A1 | 8/2005 | Eckhardt et al. | |
| 2005/0187227 | A1* | 8/2005 | Himmelsbach et al. | 514/263.22 |
| 2005/0203095 | A1 | 9/2005 | Eckhardt | |
| 2005/0234108 | A1 | 10/2005 | Himmelsbach et al. | |
| 2005/0261352 | A1 | 11/2005 | Eckhardt | |
| 2006/0004074 | A1 | 1/2006 | Eckhardt | |
| 2006/0058323 | A1* | 3/2006 | Eckhardt et al. | 514/263.22 |
| 2006/0063787 | A1 | 3/2006 | Yoshikawa | |
| 2006/0079541 | A1 | 4/2006 | Langkopf | |
| 2006/0094722 | A1 | 5/2006 | Yasuda | |
| 2006/0100199 | A1 | 5/2006 | Yoshikawa | |
| 2006/0142310 | A1* | 6/2006 | Pfrengle et al. | 514/263.22 |
| 2006/0173056 | A1 | 8/2006 | Kitajima | |
| 2006/0205711 | A1 | 9/2006 | Himmelsbach | |
| 2006/0247226 | A1 | 11/2006 | Himmelsbach | |
| 2007/0027168 | A1* | 2/2007 | Pfrengle et al. | 514/263.22 |
| 2007/0088038 | A1 | 4/2007 | Eckhardt | |
| 2007/0093659 | A1 | 4/2007 | Bonfanti | |
| 2007/0142383 | A1 | 6/2007 | Eckhardt | |
| 2007/0185091 | A1 | 8/2007 | Himmelsbach et al. | |
| 2007/0219178 | A1 | 9/2007 | Muramoto | |

FOREIGN PATENT DOCUMENTS

| | | | |
|---|---|---|---|
| CA | 2418656 | A1 | 2/2002 |
| CA | 2496325 | A1 | 3/2004 |
| CA | 2496249 | A1 | 4/2004 |
| CA | 2505389 | A1 | 5/2004 |
| CA | 2508233 | A1 | 6/2004 |
| CA | 2529729 | A1 | 12/2004 |
| CA | 2543074 | A1 | 6/2005 |
| CA | 2555050 | A1 | 9/2005 |
| CA | 2556064 | A1 | 9/2005 |
| CA | 2590912 | A1 | 6/2006 |
| DE | 10109021 | A1 | 9/2002 |
| DE | 10117803 | A1 | 10/2002 |
| EP | 0149578 | A2 | 7/1985 |
| EP | 0400974 | A2 | 5/1990 |
| EP | 0399285 | A1 | 11/1990 |
| EP | 0412358 | A1 | 2/1991 |
| EP | 0524482 | A1 | 1/1993 |
| EP | 0657454 | A1 | 6/1995 |
| EP | 1054012 | A1 | 11/2000 |
| EP | 1338595 | A2 | 8/2003 |
| EP | 1514552 | A1 | 3/2005 |
| EP | 1537880 | A1 | 8/2005 |
| ES | 385302 | A1 | 4/1973 |
| FR | 2707641 | A1 | 1/1995 |
| JP | 37-4895 | | 6/1962 |
| JP | 2003/300977 | | 10/2003 |
| JP | 2006/045156 | | 2/2006 |
| WO | 91/07945 | A1 | 6/1991 |
| WO | 94/03456 | A1 | 2/1994 |
| WO | 99/29695 | A1 | 6/1999 |
| WO | WO 02/02560 | A2 | 1/2002 |
| WO | 02/14271 | A1 | 2/2002 |
| WO | 02/24698 | A1 | 3/2002 |
| WO | WO 02/068420 | A1 | 9/2002 |
| WO | WO 03/004496 | A1 | 1/2003 |
| WO | WO 03/024965 | A2 | 3/2003 |
| WO | 03/057200 | A2 | 7/2003 |
| WO | 03/104229 | A1 | 12/2003 |
| WO | 2004/018467 | A2 | 3/2004 |
| WO | WO 2004/018468 | A2 | 3/2004 |
| WO | 2004/028524 | A1 | 4/2004 |
| WO | 2004/033455 | A2 | 4/2004 |
| WO | 2004/041820 | A1 | 5/2004 |
| WO | 2004/046148 | A1 | 6/2004 |
| WO | 2004/048379 | A1 | 6/2004 |
| WO | 2004/096806 | A1 | 11/2004 |
| WO | 2004/108730 | A1 | 12/2004 |
| WO | 2004/050658 | A1 | 6/2005 |
| WO | 2005/058901 | A1 | 6/2005 |
| WO | 2005/082906 | A1 | 9/2005 |
| WO | 2005/085246 | A1 | 9/2005 |
| WO | 2004/111051 | A1 | 12/2005 |
| WO | 2006/029769 | A1 | 3/2006 |
| WO | 2006/048427 | A1 | 5/2006 |
| WO | 2006/068163 | A1 | 6/2006 |
| WO | 2007/017423 | A2 | 2/2007 |
| WO | WO 2008/017670 | A1 | 2/2008 |

OTHER PUBLICATIONS

White, Clinical Diabetes 26:53-57, 2008.*

U.S. Appl. No. 11/744,700, filed May 4, 2007, Sieger.

U.S. Appl. No. 11/744,701, filed May 4, 2007, Kohlrausch.

U.S. Appl. No. 11/744,703, filed May 4, 2007, Dugi.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; orginally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β -Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol, 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

Office Action for U.S. Appl. No. 10/695,597 mailed May 2, 2008.

Januvia; Patient Information; Oct. 2007.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Cygankiewicz, Andrzej et al., Investigations into the Piperazine Derivatives of Dimethylxanthine:, ACTA Polon. Pharm. [Papers of Polish Pharmacology], XXXOV, No. 5, pp. 607-612, 1977.

Patani George A. et al.: "Bioisoterism : A Rational Approach in Drug Design", Chemical Reviews, 1996, vol. 96, No. 8, pp. 3147-3176.

Zejc, Alfred et al; Badania Nad Piperazynowymi Pochodnymi Dwumetyloksantyn; ACTA Polon. Pharm. XXXV. Nr 4, 1976, pp. 417-421.

* cited by examiner

8-[3-AMINO-PIPERIDIN-1-YL]-XANTHINES, THEIR PREPARATION AND THEIR USE AS PHARMACEUTICAL COMPOSITIONS

APPLICATION DATA

This application claims the benefit under 35 USC 119(a) of German Application No. 10 2004 008 112, filed Feb. 18, 2004, German Patent Application No. 10 2004 012 921, filed Mar. 17, 2004, and German Patent Application No. 10 2004 032 263, filed Jul. 3, 2004, which applications are incorporated herein by reference in their entirety. This application claims the benefit under 35 USC 119(e) of U.S. Provisional Application Ser. No. 60/551,108, filed on Mar. 8, 2004, and U.S. Provisional Application Ser. No. 60/562,573, filed on Apr. 15, 2004, which applications are incorporated herein by reference in their entirety.

FIELD OF THE INVENTION

The present invention relates to new substituted xanthines of general formula (I)

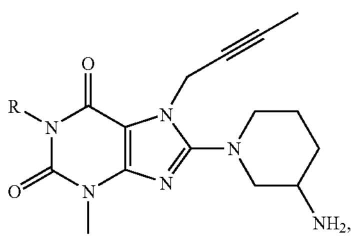

the tautomers, the enantiomers, the stereoisomers, the mixtures thereof, and the salts thereof, particularly the physiologically acceptable salts thereof, with inorganic or organic acids that have valuable pharmacological properties, particularly an inhibiting effect, on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof, and processes for the preparation thereof.

Xanthine derivatives with an inhibiting effect on DPP-IV are already known from WO 02/068420, WO 02/02560, WO 03/004496, WO 03/024965, WO 04/018468, WO 04/048379, JP 2003300977, and EP 1 338 595, which applications and other applications corresponding thereto are incorporated herein by reference in their entireties.

In the above formula I:

R denotes a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl, or 4-chlorobenzyl group, a 2-trifluoromethyl-benzyl, 3-trifluoromethyl-benzyl, or 4-trifluoromethyl-benzyl group, a 3-trifluoromethoxy-benzyl or 4-trifluoromethoxy-benzyl group, a 2-cyanobenzyl, 3-cyanobenzyl, or 4-cyanobenzyl group, a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl, or 2-cyano-4-bromobenzyl group, a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl, or 3,4-dimethoxy-6-fluoro-benzyl group, a (benzo[1,3]dioxol-5-yl)methyl group, a [(4-cyano-benzo[1,3]dioxol-5-yl)methyl group, a 2-(3-cyclopropyloxy-phenyl)-2-oxo-ethyl, 2-(3-cyclopropylmethoxy-phenyl)-2-oxo-ethyl, or 2-(3-cyclobutyloxy-phenyl)-2-oxo-ethyl group, a 2-oxo-2-[2-(pyridin-3-yl)-phenyl]-ethyl or 2-oxo-2-[2-(pyridin-4-yl)-phenyl]-ethyl group, a (3-cyano-naphthalen-1-yl)methyl, (1,4-dicyano-naphthalen-2-yl)methyl, or (2,4-dimethoxy-naphthalen-1-yl)methyl group, a (furan-2-yl)methyl, (furan-3-yl)methyl, (5-bromo-furan-2-yl)methyl, (5-methyl-furan-2-yl)methyl, (5-cyano-furan-2-yl)methyl, or (5-methoxycarbonyl-furan-2-yl)methyl group, a (pyridin-2-yl)methyl, (6-fluoro-pyridin-2-yl)methyl or (5-methoxy-pyridin-2-yl)methyl group, a (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, or (5-cyano-6-methoxy-pyridin-2-yl)methyl group, a (6-phenyl-pyridin-2-yl)methyl or a ([2,2']bipyridinyl-6-yl) methyl group, a (pyrimidin-2-yl)methyl, (4-methyl-pyrimidin-2-yl)methyl or (4,6-dimethyl-pyrimidin-2-yl)methyl group, a (2-phenyl-pyrimidin-4-yl)methyl or (4-phenyl-pyrimidin-2-yl)methyl group, a [(1-methyl-1H-benzotriazol-5-yl)methyl] group, a (6-fluoro-quinolin-2-yl)methyl, (7-fluoro-quinolin-2-yl) methyl, (2-methyl-quinolin-4-yl)methyl, (3-cyano-quinolin-2-yl)methyl, (3-cyano-4-methyl-quinolin-2-yl)methyl, (4-cyano-quinolin-2-yl)methyl, (5-cyano-quinolin-2-yl) methyl, (8-cyano-quinolin-2-yl)methyl, (6-amino-quinolin-2-yl)methyl, (8-amino-quinolin-2-yl)methyl, (4-methoxy-quinolin-2-yl)methyl, (6-methoxy-quinolin-2-yl) methyl, (6,7-dimethoxy-quinolin-2-yl)methyl, or (8-cyano-quinolin-7-yl)methyl group, a (1-cyano-isoquinolin-3-yl)methyl, (4-cyano-isoquinolin-1-yl)methyl-(4-cyano-isoquinolin-3-yl)methyl, or [(4-(pyridin-2-yl)-isoquinolin-1-yl]methyl group, a (quinazolin-6-yl)methyl, (quinazolin-7-yl)methyl, (2-methyl-quinazolin-4-yl)methyl, (4,5-dimethyl-quinazolin-2-yl)methyl, (4-ethyl-quinazolin-2-yl)methyl, (4-cyclopropyl-quinazolin-2-yl)methyl, (2-phenyl-quinazolin-4-yl) methyl, (4-cyano-quinazolin-2-yl)methyl, (4-phenylamino-quinazolin-2-yl)methyl, or (4-benzylamino-quinazolin-2-yl)methyl group, a (quinoxalin-5-yl)methyl-(quinoxalin-6-yl)methyl or (2,3-dimethyl-quinoxalin-6-yl)methyl group, or a ([1,5]naphthyridin-3-yl)methyl group, the tautomers, enantiomers, diastereomers, and the mixtures and the salts thereof.

Preferred are compounds of general formula Ia:

(Ia)

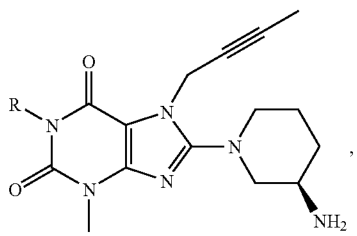

wherein R is as hereinbefore defined, as well as their tautomers and salts.

Also preferred are compounds of general formula Ib (Ib)

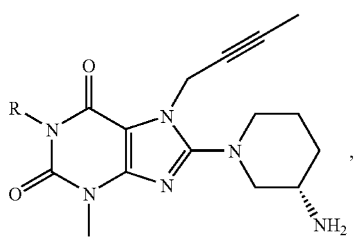

wherein R is as hereinbefore defined, as well as their tautomers and salts.

According to the invention the compounds of general formula I are obtained by methods known, per se, for example, by the following methods:

a) reacting a compound of general formula II (II)

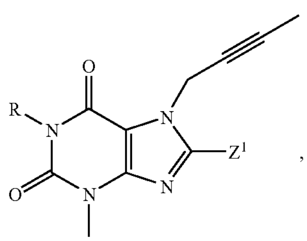

wherein

R is as hereinbefore defined and $Z^1$ denotes a leaving group, such as a halogen atom, a substituted hydroxy, mercapto, sulfinyl, sulfonyl or sulfonyloxy group, such as a chlorine or bromine atom, a methanesulfonyl, or methanesulfonyloxy group, with 3-aminopiperidine, the enantiomers or the salts thereof.

The reaction is expediently carried out in a solvent, such as isopropanol, butanol, tetrahydrofuran, dioxane, dimethylformamide, dimethylsulfoxide, ethyleneglycol monomethylether, ethyleneglycol diethylether, or sulfolane, optionally in the presence of an inorganic or tertiary organic base, e.g., sodium carbonate, potassium carbonate, or potassium hydroxide, a tertiary organic base, e.g., triethylamine, or in the presence of N-ethyl-diisopropylamine (Hünig base), while these organic bases may simultaneously also serve as solvent, and optionally in the presence of a reaction accelerator, such as an alkali metal halide or a palladium-based catalyst at temperatures between −20° C. and 180° C., but preferably at temperatures between −10° C. and 120° C. The reaction may, however, also be carried out without solvent or in an excess of the 3-aminopiperidine.

b) deprotecting a compound of general formula III (III)

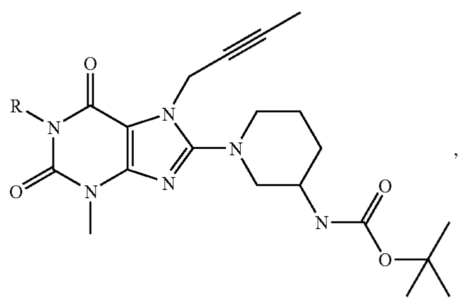

wherein R is as hereinbefore defined.

The tert.-butyloxycarbonyl group is preferably cleaved by treating with an acid, such as trifluoroacetic acid or hydrochloric acid or by treating with bromotrimethylsilane or iodotrimethylsilane, optionally using a solvent, such as methylene chloride, ethyl acetate, dioxane, methanol, isopropanol, or diethyl ether at temperatures between 0° C. and 80° C.

In the reactions described hereinbefore, any reactive groups present, such as amino, alkylamino, or imino groups, may be protected during the reaction by conventional protecting groups that are cleaved again after the reaction.

For example, a protecting group for an amino, alkylamino, or imino group may be a formyl, acetyl, trifluoroacetyl, ethoxycarbonyl, tert-butoxycarbonyl, benzyloxycarbonyl, benzyl, methoxybenzyl, or 2,4-dimethoxybenzyl group, and additionally, for the amino group, a phthalyl group.

Any protecting group used is optionally, subsequently cleaved, for example, by hydrolysis in an aqueous solvent, e.g., in water, isopropanol/water, acetic acid/water, tetrahydrofuran/water, or dioxane/water, in the presence of an acid, such as trifluoroacetic acid, hydrochloric acid, or sulfuric acid, or in the presence of an alkali metal base, such as sodium hydroxide or potassium hydroxide, or aprotically, e.g., in the presence of iodotrimethylsilane, at temperatures between 0° C. and 120° C., preferably at temperatures between 10° C. and 100° C.

However, a benzyl, methoxybenzyl, or benzyloxycarbonyl group is cleaved, for example, hydrogenolytically, e.g., with hydrogen in the presence of a catalyst, such as palladium/charcoal, in a suitable solvent, such as methanol, ethanol, ethyl acetate, or glacial acetic acid, optionally with the addition of an acid, such as hydrochloric acid, at temperatures between 0° C. and 100° C., but preferably at ambient temperatures between 20° C. and 60° C., and at a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyloxycarbonyl group is preferably cleaved by treating with an acid, such as trifluoroacetic acid or hydrochloric acid, or by treating with iodotrimethylsilane, optionally using a solvent, such as methylene chloride, dioxane, methanol, or diethyl ether.

A trifluoroacetyl group is preferably cleaved by treating with an acid, such as hydrochloric acid, optionally in the presence of a solvent, such as acetic acid, at temperatures between 50° C. and 120° C., or by treating with sodium hydroxide solution, optionally in the presence of a solvent, such as tetrahydrofuran, at temperatures between 0° C. and 50° C.

A phthalyl group is preferably cleaved in the presence of hydrazine or a primary amine, such as methylamine, ethylamine, ethanolamine, or n-butylamine, in a solvent, such as methanol, ethanol, isopropanol, toluene/water, or dioxane, at temperatures between 20° C. and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained that occur as racemates may be separated by methods known, per se, (cf. Allinger N. L. and Eliel E. L. in "Topics in Stereochemistry", Vol. 6, Wiley Interscience, 1971), into their optical enantiomers, and compounds of general formula I with at least 2 asymmetric carbon atoms may be resolved into their diastereomers on the basis of their physical-chemical differences using methods known, per se, e.g., by chromatography and/or fractional crystallisation, and, if these compounds are obtained in racemic form, they may subsequently be resolved into the enantiomers as mentioned above.

The enantiomers are preferably separated by column separation on chiral phases, or by recrystallisation from an optically active solvent, or by reacting with an optically active substance that forms salts or derivatives, such as, e.g., esters or amides with the racemic compound, particularly acids, and the activated derivatives or alcohols thereof, and separating the diastereomeric mixture of salts or derivatives thus obtained, e.g., on the basis of their differences in solubility, whereas the free antipodes may be released from the pure diastereomeric salts or derivatives by the action of suitable agents. Optically active acids in common use are, e.g., the D- and L-forms of tartaric acid, or dibenzoyltartaric acid, di-o-tolyltartaric acid, malic acid, mandelic acid, camphorsulfonic acid, glutamic acid, aspartic acid, or quinic acid. An optically active alcohol may be, for example, (+) or (−)-menthol and an optically active acyl group in amides, for example, may be a (+)- or (−)-menthyloxycarbonyl.

Furthermore, the compounds of formula I obtained may be converted into the salts thereof, particularly, for pharmaceutical use, into the physiologically acceptable salts, with inorganic or organic acids. Acids that may be used for this purpose include, for example, hydrochloric acid, hydrobromic acid, sulfuric acid, methanesulfonic acid, phosphoric acid, fumaric acid, succinic acid, lactic acid, citric acid, tartaric acid, or maleic acid.

The compounds of general formulae II and III used as starting compounds are either known from the literature or may be prepared by methods known from the literature (see Examples I to XXV).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2" that appeared in Proc. Natl. Acad. Sci. Vol. 90, pp. 5757-5761 (1993). The cell extract was obtained from cells solubilized in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 μl of substrate solution (AFC; AFC is amido-4-trifluoromethylcoumarin), final concentration 100 μM, was placed in black microtitre plates. 20 μl of assay buffer (final concentrations 50 mM Tris HCl pH 7.8, 50 mM NaCl, 1% DMSO) was pipetted therein. The reaction was started by the addition of 30 μl of solubilized Caco-2 protein (final concentration 0.14 μg of protein per well). The test substances under investigation were typically added prediluted to 20 μl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example No.) | DPP IV inhibition $IC_{50}$ [nM] |
|---|---|
| 1 | 6 |
| 1(3) | 6 |
| 1(4) | 9 |
| 1(6) | 2 |
| 1(7) | 5 |
| 1(12) | 2 |
| 1(21) | 2 |
| 1(26) | 2 |
| 1(30) | 2 |
| 1(31) | 3 |
| 1(38) | 1 |
| 1(39) | 2 |

The compounds prepared according to the invention are well tolerated, as no toxic side effects could be detected in rats after the oral administration of 10 mg/kg of the compound of Example 1(30), for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, pre-diabetes, reduced glucose tolerance or changes in the fasting blood sugar, diabetic complications (e.g., retinopathy, nephropathy, or neuropathies), metabolic acidosis or ketosis, reactive hypoglycemia, insulin resistance, metabolic syndrome, dyslipidemias of various origins, arthritis, atherosclerosis and related diseases, obesity, allograft transplantation, and osteoporosis caused by calcitonin. In addition, these substances are suitable for preventing B-cell degeneration, such as, e.g., apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides, such as, e.g., GLP-1 and GLP-2 and their link with DPP-IV inhibition, it is expected that the compounds according to the invention will be suitable for achieving, inter alla, a sedative or tranquillising effect, as well as having a favorable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases, such as, e.g., irritable bowel syndrome (IBS), Crohn's disease, or ulcerative colitis, and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand, these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as, e.g., rheumatoid arthritis, multiple sclerosis, thyroiditis, and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases, such as Alzheimer's disease, for example. The compounds described may also be used for the treatment of tumors, particularly for modifying tumor invasion and also metastasisation; examples here are their use in treating T-cell lymphomas, acute lymphoblastic leukemia, cell-based pancreatic carcinomas, basal cell carcinomas, or breast cancers. Other indications are stroke, ischemia of various origins, Parkinson's disease, and migraine. In addition, further indications include follicular and epidermal hyperkeratoses, increased keratinocyte proliferation, psoriasis, encephalomyelitis, glomerulonephritis, lipodystrophies, as well as psychosomatic, depressive, and neuropsychiatric diseases of all kinds.

The compounds according to the invention may also be used in conjunction with other active substances. Suitable therapeutic agents for such combinations include, for example, antidiabetic agents, such as metformin, sulfonylureas (e.g., glibenclamid, tolbutamide, glimepiride), nateglinide, repaglinide, thiazolidinediones (e.g., rosiglitazone, pioglitazone), PPAR-gamma agonists (e.g., GI 262570) and antagonists, PPAR-gamma/alpha modulators (e.g., KRP 297), PPAR-gamma/alpha/delta modulators, AMPK activators, ACC1 and ACC2 inhibitors, DGAT inhibitors, SMT3 receptor agonists, 11β-HSD inhibitors, FGF19 agonists or mimetics, alpha-glucosidase inhibitors (e.g., acarbose, voglibose), other DPP-IV inhibitors, alpha2 antagonists, insulin and insulin analogues, GLP-1 and GLP-1 analogues (e.g., exendin-4), or amylin. Also, combinations with SGLT2 inhibitors, such as T-1095 or KGT-1251 (869682), inhibitors of protein tyrosine phosphatase 1, substances which influence deregulated glucose production in the liver, such as, e.g., inhibitors of glucose-6-phosphatase, or fructose-1,6-bisphosphatase, glycogen phosphorylase, glucagon receptor antagonists and inhibitors of phosphoenol-pyruvate carboxykinase, glycogen synthase kinase or pyruvate dehydrokinase, lipid lowering agents, such as HMG-CoA-reductase inhibitors (e.g., simvastatin, atorvastatin), fibrates (e.g., bezafibrate, fenofibrate), nicotinic acid and its derivatives, PPAR-alpha agonists, PPAR-delta agonists, ACAT inhibitors (e.g., avasimibe), or cholesterol absorption inhibitors, such as, for example, ezetimibe, bile acid-binding substances, such as, for example, cholestyramine, inhibitors of ileac bile acid transport, HDL-raising compounds, such as, for example, inhibitors of CETP, or regulators of ABC1 or LXRalpha antagonists, LXRbeta agonists or LXRalpha/beta regulators, or active substances for the treatment of obesity, such as e.g., sibutramine or tetrahydrolipostatin, dexfenfluramine, axokine, antagonists of the cannabinoid1 receptor, MCH-1 receptor antagonists, MC4 receptor agonists, NPY5 or NPY2 antagonists, or $\beta_3$-agonists, such as SB-418790 or AD-9677, as well as agonists of the 5HT2c receptor.

It is also possible to combine the compounds with drugs for treating high blood pressure, such as, e.g., all antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances, such as hard fat or suitable mixtures thereof, into conventional galenic preparations, such as plain or coated tablets, capsules, powders, suspensions, or suppositories.

The Examples that follow are intended to illustrate the invention:

Preparation of the Starting Compounds

EXAMPLE I

1-[(4-phenylamino-quinazolin-2-yl)methyl]-3-methyl-7-(2-butyn-1-yl)-8-[3-(tert.-butyloxycarbonylamino)-piperidin-1-yl]-xanthine A mixture of 416 mg 3-methyl-7-(2-butyn-1-yl)-8-[3-(tert.-butyloxycarbonylamino)-piperidin-1-yl]-xanthine and 456 mg cesium carbonate in 4 ml N,N-dimethylformamide is stirred for 10 minutes at 80° C., then 324 mg 2-chloromethyl-4-phenylamino-quinazoline are added and the reaction mixture is stirred for two hours at 80° C. Then another 50 mg cesium carbonate and 50 mg chloromethyl-4-phenylamino-quinazoline are added and the mixture is stirred for a further 1.5 hours at 80° C. Then the solvent is distilled off and the residue is distributed between water and ethyl acetate. The organic phase is washed with dilute citric acid, water and saturated sodium chloride solution, dried over magnesium sulfate and evaporated down. The crude product is purified by chromatography over a silica gel column with ethyl acetate/petroleum ether (8:2 to 10:0) as eluant.

Yield: 425 mg (65% of theory)

$R_f$ value: 0.33 (silica gel, ethyl acetate)

Mass spectrum ($ESI^+$): m/z=650 $[M+H]^+$

The following compounds are obtained analogously to Example I:

(1) 1-[(4-benzylamino-quinazolin-2-yl)methyl]-3-methyl-7-(2-butyn-1-yl)-8-[3-(tert.-butyloxycarbonylamino)-piperidin-1-yl]-xanthine $R_f$ value: 0.20 (silica gel, ethyl acetate)

Mass spectrum ($ESI^+$): m/z=664 $[M+H]^+$ (2) 1-[(2-methyl-quinolin-4-yl)methyl]-3-methyl-7-(2-butyn-1-yl)-8-[(R)-3-(tert.-butyloxycarbonylamino)-piperidin-1-yl]-xanthine $R_f$ value: 0.80 (silica gel, methylene chloride/methanol=9:1)

Mass spectrum ($ESI^+$): m/z=572 $[M+H]^+$ (3) 1-[(3-cyano-naphthalen-1-yl)methyl]-3-methyl-7-(2-butyn-1-yl)-8-[(R)-3-(tert.-butyloxycarbonylamino)-piperidin-1-yl]-xanthine $R_f$ value: 0.67 (silica gel, methylene chloride/methanol=95:5)

Mass spectrum ($ESI^+$): m/z=582 $[M+H]^+$ (4) 1-[(2-phenyl-quinazolin-4-yl)methyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)

Mass spectrum ($ESI^+$): m/z=635 $[M+H]^+$ (5) 1-[(4-cyano-isoquinolin-1-yl)methyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/methanol/conc. aqueous ammonia=90:10:1)

Mass spectrum ($ESI^+$): m/z=583 $[M+H]^+$ (6) 1-[(4-cyano-quinolin-2-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=583 $[M+H]^+$ (7) 1-[2-(3-cyclopropyloxy-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)

Mass spectrum ($ESI^+$): m/z=591 $[M+H]^+$ (8) 1-[2-(3-cyclopropylmethoxy-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.65 (silica gel, methylene chloride/ethyl acetate=1:1)

Mass spectrum ($ESI^+$): m/z=605 $[M+H]^+$ (9) 1-[2-(3-cyclobutyloxy-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.85 (silica gel, methylene chloride/ethyl acetate=1:1)

Mass spectrum ($ESI^+$): m/z=605 $[M+H]^+$

(10) 1-[(1-cyano-isoquinolin-3-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=583 $[M+H]^+$

(11) 1-[(2,4-methoxy-naphthalen-1-yl)methyl]-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)

Mass spectrum ($ESI^+$): m/z=617 $[M+H]^+$

(12) 1-[(2,3-dimethyl-quinoxalin-6-yl)methyl]-3-methyl-7-(2-butyn-1-yl)-8-[(R)-3-(tert.-butyloxycarbonylamino)-piperidin-1-yl]-xanthine $R_f$ value: 0.50 (silica gel, ethyl acetate)

Mass spectrum ($ESI^+$): m/z=587 $[M+H]^+$

(13) 1-[(6-nitro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.45 (silica gel, ethyl acetate/petroleum ether=7:3)

Mass spectrum ($ESI^+$): m/z=603 $[M+H]^+$

(14) 1-[(quinoxalin-5-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=559 $[M+H]^+$

(15) 1-[(6-methoxy-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.65 (silica gel, ethyl acetate)

Mass spectrum ($ESI^+$): m/z=588 $[M+H]^+$

(16) 1-[(6-phenyl-pyridin-2-yl)methyl]-3-methyl-7-(2-butyn-1-yl)-8-[(R)-3-(tert.-butyloxycarbonylamino)-piperidin-1-yl]-xanthine $R_f$ value: 0.43 (silica gel, methylene chloride/methanol=96:4)

Mass spectrum ($ESI^+$): m/z=584 $[M+H]^+$

(17) 1-{[(4-(pyridin-2-yl)-isoquinolin-1-yl]methyl}-3-methyl-7-(2-butyn-1-yl)-8-[(R)-3-(tert.-butyloxycarbonylamino)-piperidin-1-yl]-xanthine

(18) 1-[(7-fluoro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.24 (silica gel, ethyl acetate/petroleum ether=1:1)

Mass spectrum ($ESI^+$): m/z=576 $[M+H]^+$

(19) 1-[(8-nitro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.63 (silica gel, methylene chloride/methanol=95:5)

Mass spectrum ($ESI^+$): m/z=603 $[M+H]^+$

(20) 1-[(6-fluoro-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.47 (silica gel, methylene chloride/methanol=95:5)

Mass spectrum ($ESI^+$): m/z=576 $[M+H]^+$

(21) 1-[2-oxo-2-(2-bromo-phenyl)-ethyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)

Mass spectrum ($ESI^+$): m/z=613, 615 $[M+H]^+$

(22) 1-cyanomethyl-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum ($ESI^+$): m/z=456 $[M+H]^+$

(23) 1-[(4-methoxy-quinolin-2-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=588 $[M+H]^+$

(24) 1-[(2-phenyl-pyrimidin-4-yl)methyl]-3-methyl-7-(2-butyn-1-yl)-8-[(R)-3-(tert.-butyloxycarbonylamino)-piperidin-1-yl]-xanthine $R_f$ value: 0.39 (silica gel, methylene chloride/methanol=96:4)

Mass spectrum ($ESI^+$): m/z=585 $[M+H]^+$

(25) 1-[([1,5]naphthyridin-3-yl)methyl]-3-methyl-7-(2-butyn-1-yl)-8-[(R)-3-(tert.-butyloxycarbonylamino)-piperidin-1-yl]-xanthine $R_f$ value: 0.28 (silica gel, ethyl acetate)

Mass spectrum ($ESI^+$): m/z=559 $[M+H]^+$

(26) 1-[(3-cyano-4-methyl-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)

Mass spectrum ($ESI^+$): m/z=597 $[M+H]^+$

(27) 1-[(4,5-dimethyl-quinazolin-2-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=587 $[M+H]^+$

(28) 1-[(5-cyano-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.42 (silica gel, petroleum ether/ethyl acetate=1:2)

Mass spectrum ($ESI^+$): m/z=583 $[M+H]^+$

(29) 1-[(3-cyano-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.80 (silica gel, methylene chloride/ethyl acetate=1:1)

(30) 1-[(4-phenyl-pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.46 (silica gel, ethyl acetate)

(31) 1-[2-(2-nitro-phenyl)-2-oxo-ethyl]-3-methyl-7-(2-butyn-1-yl)-8-[(R)-3-(tert.-butyloxycarbonylamino)-piperidin-1-yl]-xanthine $R_f$ value: 0.75 (silica gel, ethyl acetate)

Mass spectrum ($ESI^+$): m/z=580 $[M+H]^+$

(32) 1-[(1,4-dicyano-naphthalen-2-yl)methyl]-3-methyl-7-(2-butyn-1-yl)-8-[(R)-3-(tert.-butyloxycarbonylamino)-piperidin-1-yl]-xanthine $R_f$ value: 0.54 (silica gel, methylene chloride/methanol=95:5)

Mass spectrum ($ESI^+$): m/z=607 $[M+H]^+$

(33) 1-[(6,7-dimethoxy-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.36 (silica gel, ethyl acetate)

Mass spectrum ($ESI^+$): m/z=618 $[M+H]^+$

(34) 1-[(quinazolin-6-yl)methyl]-3-methyl-7-(2-butyn-1-yl)-8-[(R)-3-(tert.-butyloxycarbonylamino)-piperidin-1-yl]-xanthine $R_f$ value: 0.20 (silica gel, ethyl acetate)

Mass spectrum ($ESI^+$): m/z=559 $[M+H]^+$

(35) 1-[(4-cyano-quinazolin-2-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, methylene chloride/ethyl acetate=7:3)

Mass spectrum ($ESI^+$): m/z=584 $[M+H]^+$

(36) 1-[(quinazolin-7-yl)methyl]-3-methyl-7-(2-butyn-1-yl)-8-[(R)-3-(tert.-butyloxycarbonylamino)-piperidin-1-yl]-xanthine $R_f$ value: 0.20 (silica gel, ethyl acetate)

Mass spectrum ($ESI^+$): m/z=559 $[M+H]^+$

(37) 1-(2-cyano-benzyl)-3-methyl-7-(2-butyn-1-yl)-8-[(R)-3-(tert.-butyloxycarbonylamino)-piperidin-1-yl]-xanthine $R_f$ value: 0.50 (silica gel, methylene chloride/ethyl acetate=7:3)

Mass spectrum ($ESI^+$): m/z=532 $[M+H]^+$

(38) 1-(3-cyano-benzyl)-3-methyl-7-(2-butyn-1-yl)-8-[(R)-3-(tert.-butyloxycarbonylamino)-piperidin-1-yl]-xanthine $R_f$ value: 0.58 (silica gel, methylene chloride/ethyl acetate=1:1)

Mass spectrum ($ESI^+$): m/z=532 $[M+H]^+$

(39) 1-(4-cyano-benzyl)-3-methyl-7-(2-butyn-1-yl)-8-[(R)-3-(tert.-butyloxycarbonylamino)-piperidin-1-yl]-xanthine $R_f$ value: 0.61 (silica gel, methylene chloride/ethyl acetate=1:1)

Mass spectrum ($ESI^+$): m/z=532 $[M+H]^+$

(40) 1-[(pyridin-2-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=508 $[M+H]^+$

(41) 1-benzyl-3-methyl-7-(2-butyn-1-yl)-8-[(R)-3-(tert.-butyloxycarbonylamino)-piperidin-1-yl]-xanthine $R_f$ value: 0.70 (silica gel, methylene chloride/ethyl acetate=1:1)

Mass spectrum ($ESI^+$): m/z=507 $[M+H]^+$

(42) 1-(4-methoxy-benzyl)-3-methyl-7-(2-butyn-1-yl)-8-[(R)-3-(tert.-butyloxycarbonylamino)-piperidin-1-yl]-xanthine $R_f$ value: 0.75 (silica gel, ethyl acetate)

Mass spectrum ($ESI^+$): m/z=537 $[M+H]^+$

(43) 1-(2-chloro-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum ($ESI^+$): m/z=541, 543 $[M+H]^+$

(44) 1-(2,6-dicyano-benzyl)-3-methyl-7-(2-butyn-1-yl)-8-[(R)-3-(tert.-butyloxycarbonylamino)-piperidin-1-yl]-xanthine Mass spectrum ($ESI^+$): m/z=557 $[M+H]^+$

(45) 1-(2-cyano-4-bromo-benzyl)-3-methyl-7-(2-butyn-1-yl)-8-[(R)-3-(tert.-butyloxycarbonylamino)-piperidin-1-yl]-xanthine Mass spectrum ($ESI^+$): m/z=610, 612 $[M+H]^+$

(46) 1-(3-fluoro-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum ($ESI^+$): m/z=525 $[M+H]^+$

(47) 1-(3,5-dimethoxy-benzyl)-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)

Mass spectrum ($ESI^+$): m/z=567 $[M+H]^+$

(48) 1-(2-fluoro-benzyl)-3-methyl-7-(2-butyn-1-yl)-8-[(R)-3-(tert.-butyloxycarbonylamino)-piperidin-1-yl]-xanthine $R_f$ value: 0.85 (silica gel, ethyl acetate)

Mass spectrum ($ESI^+$): m/z=525 $[M+H]^+$

(49) 1-[(6-cyano-pyridin-2-yl)methyl]-3-methyl-7-(2-butyn-1-yl)-8-[(R)-3-(tert.-butyloxycarbonylamino)-piperidin-1-yl]-xanthine $R_f$ value: 0.60 (silica gel, methylene chloride/ethyl acetate=1:1)

Mass spectrum ($ESI^+$): m/z=533 $[M+H]^+$

(50) 1-[(3-cyano-pyridin-2-yl)methyl]-3-methyl-7-(2-butyn-1-yl)-8-[(R)-3-(tert.-butyloxycarbonylamino)-piperidin-1-yl]-xanthine $R_f$ value: 0.60 (silica gel, methylene chloride/ethyl acetate=1:1)

Mass spectrum (ESI$^+$): m/z=533 [M+H]$^+$

(51) 1-(2-cyano-3-chloro-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=566, 568 [M+H]$^+$

(52) 1-(4-fluoro-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum (ESI$^+$): m/z=525 [M+H]$^+$

(53) 1-(4-chloro-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum (ESI$^+$): m/z=541, 543 [M+H]$^+$

(54) 1-(2-cyano-4-fluoro-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=550 [M+H]$^+$

(55) 1-(3-cyano-4-fluoro-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=550 [M+H]$^+$

(56) 1-(2-chloro-4-cyano-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=566, 568 [M+H]$^+$

(57) 1-[(5-methoxycarbonyl-furan-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=555 [M+H]$^+$

(58) 1-(2-trifluoromethyl-4-cyano-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=600 [M+H]$^+$

(59) 1-(3,5-dicyano-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=557 [M+H]$^+$

(60) 1-(3-nitro-4-cyano-benzyl)-3-methyl-7-(2-butyn-1-yl)-8-[(R)-3-(tert.-butyloxycarbonylamino)-piperidin-1-yl]-xanthine Mass spectrum (ESI$^+$): m/z=577 [M+H]$^+$

(61) 1-[(2-cyano-pyridin-3-yl)methyl]-3-methyl-7-(2-butyn-1-yl)-8-[(R)-3-(tert.-butyloxycarbonylamino)-piperidin-1-yl]-xanthine $R_f$ value: 0.50 (silica gel, methylene chloride/ethyl acetate=1:1)

Mass spectrum (ESI$^+$): m/z=533 [M+H]$^+$

(62) 1-(2-cyano-4-methoxy-benzyl)-3-methyl-7-(2-butyn-1-yl)-8-[(R)-3-(tert.-butyloxycarbonylamino)-piperidin-1-yl]-xanthine $R_f$ value: 0.70 (silica gel, methylene chloride/ethyl acetate=1:1)

Mass spectrum (ESI$^+$): m/z=562 [M+H]$^+$

(63) 1-(2-cyano-5-methoxy-benzyl)-3-methyl-7-(2-butyn-1-yl)-8-[(R)-3-(tert.-butyloxycarbonylamino)-piperidin-1-yl]-xanthine $R_f$ value: 0.75 (silica gel, methylene chloride/ethyl acetate=1:1)

Mass spectrum (ESI$^+$): m/z=562 [M+H]$^+$

(64) 1-(3-methoxy-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum (ESI$^+$): m/z=537 [M+H]$^+$

(65) 1-(3-trifluoromethyl-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum (ESI$^+$): m/z=575 [M+H]$^+$

(66) 1-(3,4-dimethoxy-benzyl)-3-methyl-7-(2-butyn-1-yl)-8-[(R)-3-(tert.-butyloxycarbonylamino)-piperidin-1-yl]-xanthine $R_f$ value: 0.65 (silica gel, ethyl acetate)

Mass spectrum (ESI$^+$): m/z=567 [M+H]$^+$

(67) 1-(3-chloro-benzyl)-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum (ESI$^+$): m/z=541, 543 [M+H]$^+$

(68) 1-(4-trifluoromethyl-benzyl)-3-methyl-7-(2-butyn-1-yl)-8-[(R)-3-(tert.-butyloxycarbonylamino)-piperidin-1-yl]-xanthine $R_f$ value: 0.85 (silica gel, ethyl acetate)

Mass spectrum (ESI$^+$): m/z=575 [M+H]$^+$

(69) 1-[([2,2']bipyridinyl-6-yl)methyl]-3-methyl-7-(2-butyn-1-yl)-8-[(R)-3-(tert.-butyloxycarbonylamino)-piperidin-1-yl]-xanthine $R_f$ value: 0.53 (aluminium oxide, methylene chloride/methanol=98:2)

Mass spectrum (ESI$^+$): m/z=585 [M+H]$^+$

(70) 1-(3,4-dimethoxy-6-fluoro-benzyl)-3-methyl-7-(2-butyn-1-yl)-8-[(R)-3-(tert.-butyloxycarbonylamino)-piperidin-1-yl]-xanthine $R_f$ value: 0.65 (silica gel, ethyl acetate)

Mass spectrum (ESI$^+$): m/z=585 [M+H]$^+$

(71) 1-[(6-fluoro-pyridin-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=526 [M+H]$^+$

(72) 1-[(5-cyano-6-methoxy-pyridin-2-yl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=563 [M+H]$^+$

(73) 1-(2,6-Difluoro-benzyl)-3-methyl-7-(2-butyn-1-yl)-8-[(R)-3-(tert.-butyloxycarbonylamino)-piperidin-1-yl]-xanthine $R_f$ value: 0.62 (silica gel, ethyl acetate)

Mass spectrum (ESI$^+$): m/z=543 [M+H]$^+$

(74) 1-(3-trifluoromethoxy-benzyl)-3-methyl-7-(2-butyn-1-yl)-8-[(R)-3-(tert.-butyloxycarbonylamino)-piperidin-1-yl]-xanthine $R_f$ value: 0.67 (silica gel, ethyl acetate)

Mass spectrum (ESI$^+$): m/z=591 [M+H]$^+$

(75) 1-(4-trifluoromethoxy-benzyl)-3-methyl-7-(2-butyn-1-yl)-8-[(R)-3-(tert.-butyloxycarbonylamino)-piperidin-1-yl]-xanthine $R_f$ value: 0.62 (silica gel, ethyl acetate)

Mass spectrum (ESI$^+$): m/z=591 [M+H]$^+$

(76) 1-[(2-cyano-pyridin-4-yl)methyl]-3-methyl-7-(2-butyn-1-yl)-8-[(R)-3-(tert.-butyloxycarbonylamino)-piperidin-1-yl]-xanthine $R_f$ value: 0.55 (silica gel, methylene chloride/ethyl acetate=1:1)

Mass spectrum (ESI$^+$): m/z=533 [M+H]$^+$

(77) 1-[(5-cyano-pyridin-2-yl)methyl]-3-methyl-7-(2-butyn-1-yl)-8-[(R)-3-(tert.-butyloxycarbonylamino)-piperidin-1-yl]-xanthine $R_f$ value: 0.55 (silica gel, methylene chloride/ethyl acetate=1:1)

Mass spectrum ($ESI^+$): m/z=533 $[M+H]^+$

(78) 1-[(pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.60 (silica gel, ethyl acetate/methanol=9:1)

Mass spectrum ($ESI^+$): m/z=509 $[M+H]^+$

(79) 1-[(4-methyl-pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.60 (silica gel, ethyl acetate/methanol=9:1)

Mass spectrum ($ESI^+$): m/z=523 $[M+H]^+$

(80) 1-[(4,6-dimethyl-pyrimidin-2-yl)methyl]-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate/methanol=9:1)

Mass spectrum ($ESI^+$): m/z=537 $[M+H]^+$

(81) 1-[(quinoxalin-6-yl)methyl]-3-methyl-7-(2-butyn-1-yl)-8-bromo-xanthine $R_f$ value: 0.55 (silica gel, ethyl acetate)

Mass spectrum ($ESI^+$): m/z=439, 441 $[M+H]^+$

(82) 1-(3-fluoro-4-methoxy-benzyl)-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)

Mass spectrum ($ESI^+$): m/z=555 $[M+H]^+$

(83) 1-(3,4-difluoro-benzyl)-3-methyl-7-(2-butyn-1-yl)-8-[(R)-3-(tert.-butyloxycarbonylamino)-piperidin-1-yl]-xanthine $R_f$ value: 0.75 (silica gel, ethyl acetate)

Mass spectrum ($ESI^+$): m/z=543 $[M+H]^+$

(84) 1-(2-fluoro-5-methoxy-benzyl)-3-methyl-7-(2-butyn-1-yl)-8-[(R)-3-(tert.-butyloxycarbonylamino)-piperidin-1-yl]-xanthine $R_f$ value: 0.55 (silica gel, ethyl acetate/petroleum ether=3:2)

Mass spectrum ($ESI^+$): m/z=555 $[M+H]^+$

(85) 1-(2-fluoro-3-methoxy-benzyl)-3-methyl-7-(2-butyn-1-yl)-8-[(R)-3-(tert.-butyloxycarbonylamino)-piperidin-1-yl]-xanthine $R_f$ value: 0.48 (silica gel, ethyl acetate/petroleum ether=3:2)

Mass spectrum ($ESI^+$): m/z=555 $[M+H]^+$

(86) 1-[(4-cyano-isoquinolin-3-yl)methyl]-3-methyl-7-(2-butyn-1-yl)-8-[(R)-3-(tert.-butyloxycarbonylamino)-piperidin-1-yl]-xanthine $R_f$ value: 0.55 (silica gel, methylene chloride/methanol=95:5)

Mass spectrum ($ESI^+$): m/z=583 $[M+H]^+$

(87) 1-(2-fluoro-4-methoxy-benzyl)-3-methyl-7-(2-butyn-1-yl)-8-[(R)-3-(tert.-butyloxycarbonylamino)-piperidin-1-yl]-xanthine $R_f$ value: 0.48 (silica gel, ethyl acetate/petroleum ether=1:1)

Mass spectrum ($ESI^+$): m/z=555 $[M+H]^+$

(88) 1-[(furan-2-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=497 $[M+H]^+$

(89) 1-(3,4-dicyano-benzyl)-3-methyl-7-(2-butyn-1-yl)-8-[(R)-3-(tert.-butyloxycarbonylamino)-piperidin-1-yl]-xanthine Mass spectrum ($ESI^+$): m/z=557 $[M+H]^+$

(90) 1-(4-cyano-2-fluoro-benzyl)-3-methyl-7-(2-butyn-1-yl)-8-[(R)-3-(tert.-butyloxycarbonylamino)-piperidin-1-yl]-xanthine Mass spectrum ($ESI^+$): m/z=550 $[M+H]^+$

(91) (1-(2-cyano-5-fluoro-benzyl)-3-methyl-7-(2-butyn-1-yl)-8-[(R)-3-(tert.-butyloxycarbonylamino)-piperidin-1-yl]-xanthine Mass spectrum ($ESI^+$): m/z=550 $[M+H]^+$

(92) 1-[(5-formyl-furan-2-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=525 $[M+H]^+$

(93) 1-(2-cyano-6-fluoro-benzyl)-3-methyl-7-(2-butyn-1-yl)-8-[(R)-3-(tert.-butyloxycarbonylamino)-piperidin-1-yl]-xanthine

(94) 1-(4-cyano-3-fluoro-benzyl)-3-methyl-7-(2-butyn-1-yl)-8-[(R)-3-(tert.-butyloxycarbonylamino)-piperidin-1-yl]-xanthine Mass spectrum ($ESI^+$): m/z=550 $[M+H]^+$

(95) 1-(2-cyano-3-methoxy-benzyl)-3-methyl-7-(2-butyn-1-yl)-8-bromo-xanthine $R_f$ value: 0.85 (silica gel, ethyl acetate)

Mass spectrum ($ESI^+$): m/z=442, 444 $[M+H]^+$

(96) 1-[(8-cyano-quinolin-7-yl)methyl]-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)

Mass spectrum ($ESI^+$): m/z=583 $[M+H]^+$

(97) 1-[(4-cyano-pyridin-3-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, ethyl acetate/cyclohexane=3:1)

Mass spectrum ($ESI^+$): m/z=533 $[M+H]^+$

(98) 1-[(8-cyano-quinolin-2-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, ethyl acetate/petroleum ether=4:1)

Mass spectrum ($ESI^+$): m/z=583 $[M+H]^+$

(99) 1-[(1-methyl-1H-benzotriazol-5-yl)methyl]-3-methyl-7-(2-butyn-1-yl)-8-[(R)-3-(tert.-butyloxycarbonylamino)-piperidin-1-yl]-xanthine $R_f$ value: 0.30 (silica gel, methylene chloride/ethyl acetate=1:1)

Mass spectrum ($ESI^+$): m/z=562 $[M+H]^+$ (100) 1-[(3-cyano-pyridin-4-yl)methyl]-3-methyl-7-(2-butyn-1-yl)-8-[(R)-3-(tert.-butyloxycarbonylamino)-piperidin-1-yl]-xanthine $R_f$ value: 0.30 (silica gel, methylene chloride/ethyl acetate=1:1)

Mass spectrum ($ESI^+$): m/z=533 $[M+H]^+$ (101) 1-[(3-cyano-pyridin-2-yl)methyl]-3-methyl-7-(2-butyn-1-yl)-8-bromo-xanthine Mass spectrum ($ESI^+$): m/z=413, 415 $[M+H]^+$ (102) 1-[(4-cyano-benzo[1,3]dioxol-5-yl)methyl]-3-methyl-7-(2-butyn-1-yl)-8-[(R)-3-(tert.-butyloxycarbonylamino)-piperidin-1-yl]-xanthine $R_f$ value: 0.80 (silica gel, ethyl acetate)

Mass spectrum ($ESI^+$): m/z=576 $[M+H]^+$

EXAMPLE II

3-methyl-7-(2-butyn-1-yl)-8-[(R)-3-(tert.-butyloxycarbonylamino)-piperidin-1-yl]-xanthine 11.00 g of (R)-3-tert.-butyloxycarbonylamino-piperidine are added to 15.00 g of 3-methyl-7-(2-butyn-1-yl)-8-bromoxanthine and 16.00 g potassium carbonate in 100 ml dimethylsulfoxide and the thick light beige suspension is stirred for four hours with a mechanical stirrer at approx. 114° C. Then another 900 mg of (R)-3-tert.-butyloxycarbonylamino-piperidine, dissolved in 10 ml dimethylsulfoxide, are added to the reaction mixture and this is stirred for a further two hours at 114° C. After cooling to ambient temperature the reaction mixture is liberally diluted with water. The precipitate formed is thoroughly triturated until there are no lumps left and suction filtered. The light-colored solid is again suspended with water, suction filtered, washed with water and diethyl ether and dried in the circulating air dryer at 60° C.

Yield: 19.73 g (94% of theory)

$R_f$ value: 0.64 (silica gel, ethyl acetate)

Mass spectrum ($ESI^+$): m/z=417 $[M+H]^+$

The following compound is obtained analogously to Example II:

(1) 3-methyl-7-(2-butyn-1-yl)-8-[(3-(tert.-butyloxycarbonylamino)-piperidin-1-yl]-xanthine melting point: 235-237° C.

Mass spectrum ($ESI^+$): m/z=417 $[M+H]^+$ (2) 1-[(quinoxalin-6-yl)methyl]-3-methyl-7-(2-butyn-1-yl)-8-[(R)-3-(tert.-butyloxycarbonylamino)-piperidin-1-yl]-xanthine $R_f$ value: 0.40 (silica gel, ethyl acetate)

Mass spectrum ($ESI^+$): m/z=559 $[M+H]^+$ (3) 1-[(5-methyl-furan-2-yl)methyl]-3-methyl-7-(2-butyn-1-yl)-8-[(R)-3-(tert.-butyloxycarbonylamino)-piperidin-1-yl]-xanthine Mass spectrum ($ESI^+$): m/z=511 $[M+H]^+$ (4) 1-(2-cyano-3-methoxy-benzyl)-3-methyl-7-(2-butyn-1-yl)-8-[(R)-3-(tert.-butyloxycarbonylamino)-piperidin-1-yl]-xanthine $R_f$ value: 0.50 (silica gel, ethyl acetate)

Mass spectrum ($ESI^+$): m/z=562 $[M+H]^+$ (5) 1-[(3-cyano-pyridin-2-yl)methyl]-3-methyl-7-(2-butyn-1-yl)-8-[(S)-3-(tert.-butyloxycarbonylamino)-piperidin-1-yl]-xanthine $R_f$ value: 0.50 (silica gel, ethyl acetate)

Mass spectrum ($ESI^+$): m/z=533 $[M+H]^+$

EXAMPLE III

3-methyl-7-(2-butyn-1-yl)-8-bromo-xanthine 17.06 g 1-bromo-2-butyn are added to 30.17 g of 3-methyl-8-bromo-xanthine and 27.00 ml Hünig base in 370 ml N,N-dimethylformamide. The reaction mixture is stirred for two hours at ambient temperature, then another 1 ml of 1-bromo-2-butyne is added and the mixture is stirred for a further hour at ambient temperature. For working up the reaction mixture is diluted with approx. 300 ml water. The light-colored precipitate formed is suction filtered and washed with water. The filter cake is washed with a little ethanol and diethyl ether and dried at 60° C. in the circulating air dryer.

Yield: 30.50 g (84% of theory)

$R_f$ value: 0.24 (silica gel, methylene chloride/methanol=95:5)

Mass spectrum ($ESI^+$): m/z=297, 299 $[M+H]^+$

EXAMPLE IV

2-chloromethyl-4-phenylamino-quinazoline

Prepared by reacting 500 mg 4-chloro-2-chloromethyl-quinazoline with 438 mg aniline in 12 ml methylene chloride at ambient temperature.

Yield: 518 mg (82% of theory)

$R_f$ value: 0.60 (silica gel, cyclohexane/ethyl acetate=1:1)

Mass spectrum ($ESI^+$): m/z=270, 272 $[M+H]^+$

The following compound is obtained analogously to Example IV:

(1) 2-chloromethyl-4-benzylamino-quinazoline $R_f$ value: 0.60 (silica gel, cyclohexane/ethyl acetate=1:1)

Mass spectrum ($ESI^+$): m/z=284, 286 $[M+H]^+$

EXAMPLE V

1-bromomethyl-4-cyano-isoquinoline

Prepared by bromination of 1-methyl-4-cyano-isoquinoline with N-bromosuccinimide in the presence of azobisisobutyronitrile in carbon tetrachloride at 80° C.

$R_f$ value: 0.51 (silica gel, methylene chloride)

Mass spectrum (EI): m/z=246, 248 $[M]^+$

The following compounds are obtained analogously to Example V:

(1) 2-bromomethyl-4-cyano-quinoline

Mass spectrum ($ESI^+$): m/z=247, 249 $[M+H]^+$ (2) 3-bromomethyl-1-cyano-isoquinoline Mass spectrum ($ESI^+$): m/z=247, 249 $[M+H]^+$ (3) 1-bromomethyl-4-(pyridin-2-yl)-isoquinoline $R_f$ value: 0.47 (silica gel, methylene chloride/methanol=9:1)

(4) 2-bromomethyl-4-methoxy-quinoline

Mass spectrum ($ESI^+$): m/z=252, 254 $[M+H]^+$ (5) 3-bromomethyl-[1,5]naphthyridine Mass spectrum ($ESI^+$): m/z=223, 225 $[M+H]^+$ (6) 2-bromomethyl-5-cyano-quinoline $R_f$ value: 0.28 (silica gel, petroleum ether/ethyl acetate=5:1)

Mass spectrum ($ESI^+$): m/z=247, 249 $[M+H]^+$ (7) 2-bromomethyl-3-cyano-quinoline $R_f$ value: 0.65 (silica gel, cyclohexane/ethyl acetate=3:1)

(8) 2-bromomethyl-4-phenyl-pyrimidine $R_f$ value: 0.88 (silica gel, ethyl acetate)

Mass spectrum ($ESI^+$): m/z=249, 251 $[M+H]^+$ (9) 2-bromomethyl-1,4-dicyano-naphthalene $R_f$ value: 0.48 (silica gel, petroleum ether/ethyl acetate=9:1)

Mass spectrum ($EI^+$): m/z=270, 272 $[M]^+$

(10) 2-bromomethyl-6,7-dimethoxy-quinoline $R_f$ value: 0.70 (silica gel, methylene chloride/methanol=95:5)

Mass spectrum ($ESI^+$): m/z=282, 284 $[M+H]^+$

(11) 2-bromomethyl-4-cyano-quinazoline $R_f$ value: 0.85 (silica gel, methylene chloride/methanol=99:1)

Mass spectrum ($EI^+$): m/z=247, 249 $[M]^+$

(12) 7-bromomethyl-quinazoline $R_f$ value: 0.15 (silica gel, methylene chloride/methanol=99:1)

Mass spectrum ($ESI^+$): m/z=223, 225 $[M+H]^+$

(13) 2-trifluoromethyl-4-cyano-benzylbromide

(14) 2-bromomethyl-5-cyano-6-methoxy-pyridine

Mass spectrum ($ESI^+$): m/z=227, 229 $[M+H]^+$

(15) 3-bromomethyl-4-cyano-isoquinoline $R_f$ value: 0.43 (silica gel, petroleum ether/ethyl acetate=7:3)

(16) 7-bromomethyl-8-cyano-quinoline $R_f$ value: 0.25 (silica gel, petroleum ether/ethyl acetate=7:3)

Mass spectrum ($ESI^+$): m/z=247, 249 $[M+H]^+$

(17) 2-bromomethyl-8-cyano-quinoline $R_f$ value: 0.75 (silica gel, methylene chloride/methanol=99:1)

Mass spectrum (ESI$^+$): m/z=247, 249 [M+H]$^+$

EXAMPLE VI 2-bromo-1-(3-cyclopropyloxy-phenyl)-ethanone

Prepared by bromination of 1-(3-cyclopropyloxy-phenyl)-ethanone with phenyltrimethylammonium tribromide in methylene chloride at reflux temperature.

$R_f$ value: 0.75 (silica gel, cyclohexane/ethyl acetate=3:1)

Mass spectrum (ESI$^+$): m/z=255, 257 [M+H]$^+$

The following compounds are obtained analogously to Example VI:

(1) 2-bromo-1-(3-cyclopropylmethoxy-phenyl)-ethanone $R_f$ value: 0.70 (silica gel, cyclohexane/ethyl acetate=3:1)

(2) 2-bromo-1-(3-cyclobutyloxy-phenyl)-ethanone $R_f$ value: 0.70 (silica gel, cyclohexane/ethyl acetate=3:1)

EXAMPLE VII 1-(3-cyclopropyloxy-phenyl)-ethanone

Prepared by reacting 3-hydroxyacetophenone with bromocyclopropane in the presence of potassium iodide and potassium-tert.butoxide in N,N-dimethylformamide in the microwave at 220° C.

$R_f$ value: 0.65 (silica gel, cyclohexane/ethyl acetate=3:1)

Mass spectrum (ESI$^+$): m/z=177 [M+H]$^+$

The following compounds are obtained analogously to Example VII:

(1) 1-(3-cyclopropylmethoxy-phenyl)-ethanone $R_f$ value: 0.70 (silica gel, cyclohexane/ethyl acetate=3:1)

Mass spectrum (ESI$^+$): m/z=191 [M+H]$^+$ (2) 1-(3-cyclobutyloxy-phenyl)-ethanone $R_f$ value: 0.65 (silica gel, cyclohexane/ethyl acetate=3:1)

Mass spectrum (ESI$^+$): m/z=191 [M+H]$^+$

EXAMPLE VIII 1-chloromethyl-2,4-dimethoxy-naphthalene

Prepared by chlorinating 1-hydroxymethyl-2,4-dimethoxy-naphthalene with thionyl chloride in methylene chloride at ambient temperature.

$R_f$ value: 0.78 (silica gel, cyclohexane/ethyl acetate=1:1)

Mass spectrum (EI): m/z=236, 238 [M]$^+$

EXAMPLE IX 1-hydroxymethyl-2,4-dimethoxy-naphthalene

Prepared by reducing 2,4-dimethoxy-naphthalene-1-carboxaldehyde with sodium borohydride in a mixture of dioxane and water (3:1) at ambient temperature.

$R_f$ value: 0.48 (silica gel, cyclohexane/ethyl acetate=1:1)

EXAMPLE X

1-[(6-amino-quinol in-2-yl)methyl]-3-methyl-7-(2-butyn-1-yl)-8-[(R)-3-(tert.-butyloxycarbonylamino)-piperidin-1-yl]-xanthine Prepared by treating 1-[(6-nitro-quinolin-2-yl)methyl]-3-methyl-7-(2-butyn-1-yl)-8-[(R)-3-(tert.-butyloxycarbonylamino)-piperidin-1-yl]-xanthine with sodium dithionite in a mixture of ethanol/water (5:2) at 55-60° C.

$R_f$ value: 0.40 (silica gel, methylene chloride/methanol=95:5)

Mass spectrum (ESI$^+$): m/z=573 [M+H]$^+$

EXAMPLE XI 1-methyl-4-(pyridin-2-yl)-isoquinoline

Prepared by reacting 4-bromo-1-methyl-isoquinoline with lithium-triisopropoxy-2-pyridinyl-boronate in the presence of tetrakis(triphenylphosphine)palladium, triphenylphosphine, sodium carbonate, and copper(I)iodide in 1,4-dioxane at reflux temperature.

$R_f$ value: 0.22 (silica gel, methylene chloride/methanol=95:5)

Mass spectrum (ESI$^+$): m/z=221 [M+H]$^+$

EXAMPLE XII

1-[(8-amino-quinolin-2-yl)methyl]-3-methyl-7-(2-butyn-1-yl)-8-[(R)-3-(tert.-butyloxycarbonylamino)-piperidin-1-yl]-xanthine Prepared by treating 1-[(8-nitro-quinolin-2-yl)methyl]-3-methyl-7-(2-butyn-1-yl)-8-[(R)-3-(tert.-butyloxycarbonylamino)-piperidin-1-yl]-xanthine with iron powder in a mixture of glacial acetic acid, ethanol and water (2:20:5) at reflux temperature.

$R_f$ value: 0.50 (silica gel, methylene chloride/methanol=95:5)

Mass spectrum (ESI$^+$): m/z=573 [M+H]$^+$

EXAMPLE XIII

1-{2-oxo-2-[2-(pyridin-3-yl)-phenyl]-ethyl}-3-methyl-7-(2-butyn-1-yl)-8-[(R)-3-(tert.-butyloxycarbonylamino)-piperidin-1-yl]-xanthine Prepared by reacting 1-[2-oxo-2-(2-bromo-phenyl)-ethyl]-3-methyl-7-(2-butyn-1-yl)-8-[(R)-3-(tert.-butyloxycarbonylamino)-piperidin-1-yl]-xanthine with pyridine-3-boric acid in the presence of tetrakis(triphenylphosphine) palladium, tetra-n-butylammonium bromide and sodium carbonate in a mixture of toluene/ethanol (1:1) at 105° C.

$R_f$ value: 0.55 (silica gel, ethyl acetate)

Mass spectrum (ESI$^+$): m/z=612 [M+H]$^+$

The following compound is obtained analogously to Example XII:

(1) 1-{2-oxo-2-[2-(pyridin-4-yl)-phenyl]-ethyl}-3-methyl-7-(2-butyn-1-yl)-8-[(R)-3-(tert.-butyloxycarbonylamino)-piperidin-1-yl]-xanthine (The reaction is carried out with 4-(4,4,5,5-tetramethyl-[1,3,2]dioxaborolan-2-yl)-pyridine).

$R_f$ value: 0.40 (silica gel, ethyl acetate)

Mass spectrum (ESI$^+$): m/z=612 [M+H]$^+$

EXAMPLE XIV

1-[(4-ethyl-quinazolin-2-yl)methyl]-3-methyl-7-(2-butyn-1-yl)-8-[(R)-3-(tert.-butyloxycarbonylamino)-piperidin-1-yl]-xanthine Prepared by treating 1-cyanomethyl-3-methyl-7-(2-butyn-1-yl)-8-[(R)-3-(tert.-butyloxycarbonylamino)-piperidin-1-yl]-xanthine with potassium-tert.-butoxide in methanol and subsequently reacting the resulting iminoester with 2-amino-propiophenone in the presence of glacial acetic acid.

$R_f$ value: 0.60 (silica gel, ethyl acetate)

Mass spectrum ($ESI^+$): m/z=587 $[M+H]^+$

The following compound is obtained analogously to Example XIV:

(1) 1-[(4-cyclopropyl-quinazolin-2-yl)methyl]-3-methyl-7-(2-butyn-1-yl)-8-[(R)-3-(tert.-butyloxycarbonylamino)-piperidin-1-yl]-xanthine $R_f$ value: 0.70 (silica gel, ethyl acetate)

Mass spectrum ($ESI^+$): m/z=599 $[M+H]^+$

EXAMPLE XV 2-chloromethyl-3-cyano-4-methyl-quinoline

Prepared by reacting 3-cyano-2,4-dimethyl-1-oxy-quinoline with benzosulfonic acid chloride in toluene at 80° C.

$R_f$ value: 0.55 (silica gel, cyclohexane/ethyl acetate=2:1)

Mass spectrum ($ESI^+$): m/z=217, 219 $[M+H]^+$

EXAMPLE XVI 3-cyano-2,4-dimethyl-1-oxy-quinoline

Prepared by treating 3-cyano-2,4-dimethyl-quinoline with aqueous hydrogen peroxide solution (35%) in glacial acetic acid at 60° C.

$R_f$ value: 0.35 (silica gel, ethyl acetate)

Mass spectrum ($ESI^+$): m/z=199 $[M+H]^+$

EXAMPLE XVII 2-chloromethyl-4,5-dimethyl-quinazoline

Prepared by reacting 1-(2-amino-6-methyl-phenyl)-ethanone with chloroacetonitrile in dioxane while piping in hydrogen chloride at 30-38° C.

Mass spectrum ($ESI^+$): m/z=207, 209 $[M+H]^+$

EXAMPLE XVIII

1-[(2-methyl-quinazolin-4-yl)methyl]-3-methyl-7-(2-butyn-1-yl)-8-[(R)-3-(tert.-butyloxycarbonylamino)-piperidin-1-yl]-xanthine Prepared by reacting 1-[2-(2-acetylamino-phenyl)-2-oxo-ethyl]-3-methyl-7-(2-butyn-1-yl)-8-[(R)-3-(tert.-butyloxy-carbonylamino)-piperidin-1-yl]-xanthine with ethanolic ammonia (6 M) and ammonium chloride in the autoclave at 150° C.

$R_f$ value: 0.35 (silica gel, ethyl acetate)

Mass spectrum ($ESI^+$): m/z=573 $[M+H]^+$

EXAMPLE XIX

1-[2-(2-acetylamino-phenyl)-2-oxo-ethyl]-3-methyl-7-(2-butyn-1-yl)-8-[(R)-3-(tert.-butyloxycarbonylamino)-piperidin-1-yl]-xanthine Prepared by reacting 1-[2-(2-amino-phenyl)-2-oxo-ethyl]-3-methyl-7-(2-butyn-1-yl)-8-[(R)-3-(tert.-butyloxycarbonylamino)-piperidin-1-yl]-xanthine with acetyl chloride in the presence of pyridine in methylene chloride at ambient temperature.

$R_f$ value: 0.79 (silica gel, ethyl acetate)

Mass spectrum ($ESI^+$): m/z=592 $[M+H]^+$

EXAMPLE XX

1-[2-(2-amino-phenyl)-2-oxo-ethyl]-3-methyl-7-(2-butyn-1-yl)-8-[(R)-3-(tert.-butyloxycarbonylamino)-piperidin-1-yl]-xanthine Prepared by reducing 1-[2-(2-nitro-phenyl)-2-oxo-ethyl]-3-methyl-7-(2-butyn-1-yl)-8-[(R)-3-(tert.-butyloxycarbonylamino)-piperidin-1-yl]-xanthine with tin(II)chloride dihydrate in tetrahydrofuran at ambient temperature.

$R_f$ value: 0.85 (silica gel, ethyl acetate)

Mass spectrum ($ESI^+$): m/z=550 $[M+H]^+$

EXAMPLE XXI

1-[(furan-3-yl)methyl]-3-methyl-7-(2-butyn-1-yl)-8-[(R)-3-(tert.-butyloxycarbonyl-amino)-piperidin-1-yl]-xanthine A mixture of 300 mg of 3-methyl-7-(2-butyn-1-yl)-8-[(R)-3-(tert.-butyloxycarbonyl-amino)-piperidin-1-yl]-xanthine, 95 μl furan-3-yl-methanol, 302 mg triphenylphosphine and 226 μl diisopropyl azodicarboxylate in 4 ml tetrahydrofuran is stirred overnight at ambient temperature. For working up the reaction mixture is combined with saturated potassium carbonate solution and extracted with ethyl acetate. The combined organic phases are dried over magnesium sulfate and evaporated down. The flask residue is chromatographed over a silica gel column with cyclohexane/ethyl acetate (1:1 to 3:7).

Yield: 330 mg (92% of theory)

Mass spectrum ($ESI^+$): m/z=497 $[M+H]^+$

The following compounds are obtained analogously to Example XXI:

(1) 1-[(5-methyl-furan-2-yl)methyl]-3-methyl-7-(2-butyn-1-yl)-8-bromo-xanthine

Mass spectrum ($ESI^+$): m/z=391, 393 $[M+H]^+$ (2) 1-[(5-bromo-furan-2-yl)methyl]-3-methyl-7-(2-butyn-1-yl)-8-[(R)-3-(tert.-butyloxy-carbonylamino)-piperidin-1-yl]-xanthine Mass spectrum ($ESI^+$): m/z=575, 577 $[M+H]^+$

EXAMPLE XXII

1-[(5-cyano-furan-2-yl)methyl]-3-methyl-7-(2-butyn-1-yl)-8-[(R)-3-(tert.-butyloxy-carbonylamino)-piperidin-1-yl]-xanthine Prepared by reacting 1-[(5-formyl-furan-2-yl)methyl]-3-methyl-7-(2-butyn-1-yl)-8-[(R)-3-(tert.-butyloxycarbonylamino)-piperidin-1-yl]-xanthine with hydroxylamine-O-sulfonic acid and pyridine in toluene at reflux temperature.

EXAMPLE XXIII 5-(methanesulfonyloxymethyl)-2-furan-carboxaldehyde

Prepared by reacting 5-(hydroxymethyl)-2-furan-carboxaldehyde with methanesulfonic acid chloride in the presence of triethylamine in methylene chloride at ambient temperature. The crude product is further reacted without any more purification.

EXAMPLE XXIV 2-chloromethyl-3-cyano-pyridine

Prepared from 2-(hydroxymethyl)-nicotinamide by reaction with thionyl chloride in acetonitrile and subsequent dehydration of the 2-(chloromethyl)-nicotinamide thus obtained with trifluoroacetic acid anhydride in the presence of triethylamine in methylene chloride.

Alternatively the compound is also obtained in one step by refluxing 2-(hydroxy-methyl)-nicotinamide with phosphorus oxychloride.

$R_f$ value: 0.85 (silica gel, methylene chloride/methanol=9:1)

Mass spectrum (ESI$^+$): m/z=153, 155 [M+H]$^+$

EXAMPLE XXV 8-cyano-7-methyl-quinoline

Prepared by reacting 8-bromo-7-methyl-quinoline with zinc cyanide in the presence of tetrakis(triphenylphosphine) palladium in N-methylpyrrolidinone under a protective gas atmosphere at 100-105° C.

$R_f$ value: 0.35 (silica gel, petroleum ether/ethyl acetate=7:3)

Mass spectrum (ESI$^+$): m/z=169 [M+H]$^+$

EXAMPLE XXVI 2-methyl-8-cyano-quinoline

Prepared by reacting 2-methyl-8-bromo-quinoline with copper(I)cyanide in N-methylpyrrolidinone under a protective gas atmosphere at 180° C.

$R_f$ value: 0.40 (silica gel, petroleum ether/ethyl acetate=7:3)

Mass spectrum (ESI$^+$): m/z=169 [M+H]$^+$

Preparation of the Final Compounds

EXAMPLE 1

1-[(4-phenylamino-quinazolin-2-yl)methyl]-3-methyl-7-(2-butyn-1-yl)-8-(3-amino-piperidin-1-yl)-xanthine A mixture of 400 mg 1-[(4-phenylamino-quinazolin-2-yl) methyl]-3-methyl-7-(2-butyn-1-yl)-8-[3-(tert.-butyloxycarbonylamino)-piperidin-1-yl]-xanthine in 10 ml methylene chloride is combined with 2 ml isopropanolic hydrochloric acid (5-6 M) and stirred for three hours at ambient temperature. Then the reaction mixture is diluted with methylene chloride, combined with ice water and made alkaline with 3 M potassium carbonate solution. The aqueous phase is extracted with methylene chloride. The combined extracts are washed with water, dried over magnesium sulfate and evaporated down. The flask residue is stirred with diethyl ether, suction filtered, washed with diethyl ether and dried in vacuo.

Yield: 274 mg (81% of theory)

$R_f$ value: 0.50 (silica gel, methylene chloride/methanol/conc. aqueous ammonia=90:10:0.1)

Mass spectrum (ESI$^+$): m/z=550 [M+H]$^+$

The following compounds are obtained analogously to Example 1:

(1) 1-[(4-benzylamino-quinazolin-2-yl)methyl]-3-methyl-7-(2-butyn-1-yl)-8-(3-amino-piperidin-1-yl)-xanthine $R_f$ value: 0.43 (silica gel, methylene chloride/methanol/conc. aqueous ammonia=90:10:0.1)

Mass spectrum (ESI$^+$): m/z=564 [M+H]$^+$ (2) 1-[(2-methyl-quinolin-4-yl)methyl]-3-methyl-7-(2-butyn-1-yl)-8-((R)-3-amino-piperidin-1-yl)-xanthine Mass spectrum (ESI$^+$): m/z=472 [M+H]$^+$ (3) 1-[(3-cyano-naphthalen-1-yl)methyl]-3-methyl-7-(2-butyn-1-yl)-8-((R)-3-amino-piperidin-1-yl)-xanthine $R_f$ value: 0.55 (silica gel, methylene chloride/methanol/conc. aqueous ammonia=90:10:1)

Mass spectrum (ESI$^+$): m/z=482 [M+H]$^+$ (4) 1-[(2-phenyl-quinazolin-4-yl)methyl]-3-methyl-7-(2-butyn-1-yl)-8-((R)-3-amino-piperidin-1-yl)-xanthine $R_f$ value: 0.45 (reversed phase ready-made TLC plate (E. Merck), acetonitrile/water/trifluoroacetic acid=50:50:1)

Mass spectrum (ESI$^+$): m/z=535 [M+H]$^+$ (5) 1-[(4-cyano-isoquinolin-1-yl)methyl]-3-methyl-7-(2-butyn-1-yl)-8-((R)-3-amino-piperidin-1-yl)-xanthine $R_f$ value: 0.15 (silica gel, methylene chloride/methanol/conc. aqueous ammonia=90:10:1)

Mass spectrum (ESI$^+$): m/z=483 [M+H]$^+$ (6) 1-[(4-cyano-quinolin-2-yl)methyl]-3-methyl-7-(2-butyn-1-yl)-8-((R)-3-amino-piperidin-1-yl)-xanthine Mass spectrum (ESI$^+$): m/z=483 [M+H]$^+$ (7) 1-[2-(3-cyclopropyloxy-phenyl)-2-oxo-ethyl]-3-methyl-7-(2-butyn-1-yl)-8-((R)-3-amino-piperidin-1-yl)-xanthine $R_f$ value: 0.45 (reversed phase ready-made TLC plate (E. Merck), acetonitrile/water/trifluoroacetic acid=50:50:1)

Mass spectrum (ESI$^+$): m/z=491 [M+H]$^+$ (8) 1-[2-(3-cyclopropylmethoxy-phenyl)-2-oxo-ethyl]-3-methyl-7-(2-butyn-1-yl)-8-((R)-3-amino-piperidin-1-yl)-xanthine $R_f$ value: 0.35 (reversed phase ready-made TLC plate (E. Merck), acetonitrile/water/trifluoroacetic acid=50:50:1)

Mass spectrum (ESI$^+$): m/z=505 [M+H]$^+$ (9) 1-[2-(3-cyclobutyloxy-phenyl)-2-oxo-ethyl]-3-methyl-7-(2-butyn-1-yl)-8-((R)-3-amino-piperidin-1-yl)-xanthine $R_f$ value: 0.40 (reversed phase ready-made TLC plate (E. Merck), acetonitrile/water/trifluoroacetic acid=50:50:1)

Mass spectrum (ESI$^+$): m/z=505 [M+H]$^+$

(10) 1-[(1-cyano-isoquinolin-3-yl)methyl]-3-methyl-7-(2-butyn-1-yl)-8-((R)-3-amino-piperidin-1-yl)-xanthine Mass spectrum (ESI$^+$): m/z=483 [M+H]$^+$

(11) 1-[(2,4-methoxy-naphthalen-1-yl)methyl]-3-methyl-7-(2-butyn-1-yl)-8-((R)-3-amino-piperidin-1-yl)-xanthine $R_f$ value: 0.55 (silica gel, methylene chloride/methanol/conc. aqueous ammonia=90:10:0.1)

Mass spectrum (ESI$^+$): m/z=517 [M+H]$^+$

(12) 1-[(2,3-dimethyl-quinoxalin-6-yl)methyl]-3-methyl-7-(2-butyn-1-yl)-8-((R)-3-amino-piperidin-1-yl)-xanthine $R_f$ value: 0.48 (silica gel, methylene chloride/methanol/conc. aqueous ammonia=90:10:0.1)

Mass spectrum (ESI$^+$): m/z=487 [M+H]$^+$

(13) 1-[(6-amino-quinolin-2-yl)methyl]-3-methyl-7-(2-butyn-1-yl)-8-((R)-3-amino-piperidin-1-yl)-xanthine $R_f$ value: 0.40 (silica gel, methylene chloride/methanol/conc. aqueous ammonia=90:10:0.1)

Mass spectrum (ESI$^+$): m/z=473 [M+H]$^+$

(14) 1-[(quinoxalin-5-yl)methyl]-3-methyl-7-(2-butyn-1-yl)-8-((R)-3-amino-piperidin-1-yl)-xanthine-hydrochloride Mass spectrum (ESI$^+$): m/z=459 [M+H]$^+$

(15) 1-[(6-methoxy-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)

Mass spectrum (ESI$^+$): m/z=488 [M+H]$^+$

(16) 1-[(6-phenyl-pyridin-2-yl)methyl]-3-methyl-7-(2-butyn-1-yl)-8-((R)-3-amino-piperidin-1-yl)-xanthine $R_f$ value: 0.37 (silica gel, methylene chloride/methanol/conc. aqueous ammonia=90:10:1)

Mass spectrum (ESI$^+$): m/z=484 [M+H]$^+$

(17) 1-{[(4-(pyridin-2-yl)-isoquinolin-1-yl]methyl}-3-methyl-7-(2-butyn-1-yl)-8-((R)-3-amino-piperidin-1-yl)-xanthine $R_f$ value: 0.37 (silica gel, methylene chloride/methanol/conc. aqueous ammonia=80:20:1)

Mass spectrum (ESI$^+$): m/z=535 [M+H]$^+$

(18) 1-[(7-fluoro-quinolin-2-yl)methyl]-3-methyl-7-(2-butyn-1-yl)-8-((R)-3-amino-piperidin-1-yl)-xanthine $R_f$ value: 0.58 (silica gel, methylene chloride/methanol/conc. aqueous ammonia=90:10:1)

Mass spectrum (ESI$^+$): m/z=476 [M+H]$^+$

(19) 1-[(8-amino-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)

Mass spectrum (ESI$^+$): m/z=473 [M+H]$^+$

(20) 1-[(6-fluoro-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)

Mass spectrum (ESI$^+$): m/z=476 [M+H]$^+$

(21) 1-{2-oxo-2-[2-(pyridin-3-yl)-phenyl]-ethyl}-3-methyl-7-(2-butyn-1-yl)-8-((R)-3-amino-piperidin-1-yl)-xanthine $R_f$ value: 0.55 (reversed phase ready-made TLC plate (E. Merck), acetonitrile/water/trifluoroacetic acid=50:50:1)

Mass spectrum (ESI$^+$): m/z=512 [M+H]$^+$

(22) 1-[(4-ethyl-quinazolin-2-yl)methyl]-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:0.1)

Mass spectrum (ESI$^+$): m/z=487 [M+H]$^+$

(23) 1-[(4-cyclopropyl-quinazolin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum (ESI$^+$): m/z=499 [M+H]$^+$

(24) 1-[(4-methoxy-quinolin-2-yl)methyl]-3-methyl-7-(2-butyn-1-yl)-8-((R)-3-amino-piperidin-1-yl)-xanthine Mass spectrum (ESI$^+$): m/z=488 [M+H]$^+$

(25) 1-[(2-phenyl-pyrimidin-4-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)

Mass spectrum (ESI$^+$): m/z=485 [M+H]$^+$

(26) 1-[([1,5]naphthyridin-3-yl)methyl]-3-methyl-7-(2-butyn-1-yl)-8-((R)-3-amino-piperidin-1-yl)-xanthine $R_f$ value: 0.52 (silica gel, methylene chloride/methanol/conc. aqueous ammonia=90:10:1)

Mass spectrum (ESI$^+$): m/z=459 [M+H]$^+$

(27) 1-[(3-cyano-4-methyl-quinolin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.50 (reversed phase ready-made TLC plate (E. Merck), acetonitrile/water/trifluoroacetic acid=50:50:1)

Mass spectrum (ESI$^+$): m/z=497 [M+H]$^+$

(28) 1-[(4,5-dimethyl-quinazolin-2-yl)methyl]-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=487 [M+H]$^+$

(29) 1-[(5-cyano-quinolin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)

Mass spectrum (ESI$^+$): m/z=483 [M+H]$^+$

(30) 1-[(3-cyano-quinolin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.50 (reversed phase ready-made TLC plate (E. Merck), acetonitrile/water/trifluoroacetic acid=50:50:1)

Mass spectrum (ESI$^+$): m/z=483 [M+H]$^+$

(31) 1-[(4-phenyl-pyrimidin-2-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)

Mass spectrum (ESI$^+$): m/z=485 [M+H]$^+$

(32) 1-[(2-methyl-quinazolin-4-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.38 (silica gel, methylene chloride/methanol/conc. aqueous ammonia=90:10:1)

Mass spectrum (ESI$^+$): m/z=473 [M+H]$^+$

(33) 1-[(1,4-dicyano-naphthalen-2-yl)methyl]-3-methyl-7-(2-butyn-1-yl)-8-((R)-3-amino-piperidin-1-yl)-xanthine-hydrochloride $R_f$ value: 0.86 (silica gel, methylene chloride/methanol/conc. aqueous ammonia=90:10:1)

Mass spectrum (ESI$^+$): m/z=507 [M+H]$^+$

(34) 1-{2-oxo-2-[2-(pyridin-4-yl)-phenyl]-ethyl}-3-methyl-7-(2-butyn-1-yl)-8-((R)-3-amino-piperidin-1-yl)-xanthine (BOC cleaving carried out with trifluoroacetic acid)

$R_f$ value: 0.55 (reversed phase ready-made TLC plate (E. Merck), acetonitrile/water/trifluoroacetic acid=50:50:1)

Mass spectrum (ESI$^+$): m/z=512 [M+H]$^+$

(35) 1-[(6,7-dimethoxy-quinolin-2-yl)methyl]-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:1)

Mass spectrum (ESI$^+$): m/z=518 [M+H]$^+$

(36) 1-[(quinazolin-6-yl)methyl]-3-methyl-7-(2-butyn-1-yl)-8-((R)-3-amino-piperidin-1-yl)-xanthine-hydrochloride $R_f$ value: 0.50 (silica gel, methylene chloride/methanol/conc. aqueous ammonia=90:10:0.1)

Mass spectrum (ESI$^+$): m/z=459 [M+H]$^+$

(37) 1-[(4-cyano-quinazolin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.50 (silica gel, methylene chloride/methanol/conc. aqueous ammonia=90:10:1)

Mass spectrum (ESI$^+$): m/z=484 [M+H]$^+$

(38) 1-[(quinazolin-7-yl)methyl]-3-methyl-7-(2-butyn-1-yl)-8-((R)-3-amino-piperidin-1-yl)-xanthine $R_f$ value: 0.43 (silica gel, methylene chloride/methanol/conc. aqueous ammonia=90:10:0.1)

Mass spectrum ($ESI^+$): m/z=459 $[M+H]^+$

(39) 1-(2-cyano-benzyl)-3-methyl-7-(2-butyn-1-yl)-8-((R)-3-amino-piperidin-1-yl)-xanthine (BOC cleaving carried out with trifluoroacetic acid)

$R_f$ value: 0.35 (silica gel, methylene chloride/methanol/conc. aqueous ammonia=90:10:1)

Mass spectrum ($ESI^+$): m/z=432 $[M+H]^+$

(40) 1-(3-cyano-benzyl)-3-methyl-7-(2-butyn-1-yl)-8-((R)-3-amino-piperidin-1-yl)-xanthine (BOC cleaving carried out with trifluoroacetic acid)

$R_f$ value: 0.40 (silica gel, methylene chloride/methanol/conc. aqueous ammonia=90:10:1)

Mass spectrum ($ESI^+$): m/z=432 $[M+H]^+$

(41) 1-(4-cyano-benzyl)-3-methyl-7-(2-butyn-1-yl)-8-((R)-3-amino-piperidin-1-yl)-xanthine (BOC cleaving carried out with trifluoroacetic acid)

$R_f$ value: 0.31 (silica gel, methylene chloride/methanol/conc. aqueous ammonia=90:10:1)

Mass spectrum ($ESI^+$): m/z=432 $[M+H]^+$

(42) 1-[(pyridin-2-yl)methyl]-3-methyl-7-(2-butyn-1-yl)-8-((R)-3-amino-piperidin-1-yl)-xanthine $R_f$ value: 0.52 (silica gel, methylene chloride/methanol/conc. aqueous ammonia=90:10:1)

Mass spectrum ($ESI^+$): m/z=408 $[M+H]^+$

(43) 1-benzyl-3-methyl-7-(2-butyn-1-yl)-8-((R)-3-amino-piperidin-1-yl)-xanthine (BOC cleaving carried out with trifluoroacetic acid)

melting point: 207-209° C.

Mass spectrum ($ESI^+$): m/z=407 $[M+H]^+$

(44) 1-(4-methoxy-benzyl)-3-methyl-7-(2-butyn-1-yl)-8-((R)-3-amino-piperidin-1-yl)-xanthine-hydrochloride $R_f$ value: 0.50 (silica gel, methylene chloride/methanol/conc. aqueous ammonia=90:10:0.1)

Mass spectrum ($ESI^+$): m/z=437 $[M+H]^+$

(45) 1-(2-chloro-benzyl)-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)

Mass spectrum ($ESI^+$): m/z=441, 443 $[M+H]^+$

(46) 1-(2,6-dicyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=457 $[M+H]^+$

(47) 1-(2-cyano-4-bromo-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=510, 512 $[M+H]^+$

(48) 1-(3-fluoro-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum ($ESI^+$): m/z=425 $[M+H]^+$

(49) 1-(3,5-dimethoxy-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum ($ESI^+$): m/z=467 $[M+H]^+$

(50) 1-(2-fluoro-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum ($ESI^+$): m/z=425 $[M+H]^+$

(51) 1-[(6-cyano-pyridin-2-yl)methyl]-3-methyl-7-(2-butyn-1-yl)-8-((R)-3-amino-piperidin-1-yl)-xanthine (BOC cleaving carried out with trifluoroacetic acid)

Mass spectrum ($ESI^+$): m/z=433 $[M+H]^+$

(52) 1-[(3-cyano-pyridin-2-yl)methyl]-3-methyl-7-(2-butyn-1-yl)-8-((R)-3-amino-piperidin-1-yl)-xanthine (BOC cleaving carried out with trifluoroacetic acid)

Mass spectrum ($ESI^+$): m/z=433 $[M+H]^+$

(53) 1-(2-cyano-3-chloro-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=466, 468 $[M+H]^+$

(54) 1-(4-fluoro-benzyl)-3-methyl-7-(2-butyn-1-yl)-8-((R)-3-amino-piperidin-1-yl)-xanthine (BOC cleaving carried out with trifluoroacetic acid)

Mass spectrum ($ESI^+$): m/z=425 $[M+H]^+$

(55) 1-(4-chloro-benzyl)-3-methyl-7-(2-butyn-1-yl)-8-((R)-3-amino-piperidin-1-yl)-xanthine (BOC cleaving carried out with trifluoroacetic acid)

Mass spectrum ($ESI^+$): m/z=441, 443 $[M+H]^+$

(56) 1-(2-cyano-4-fluoro-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=450 $[M+H]^+$

(57) 1-(3-cyano-4-fluoro-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=450 $[M+H]^+$

(58) 1-(2-chloro-4-cyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=466, 468 $[M+H]^+$

(59) 1-[(5-methoxycarbonyl-furan-2-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=455 $[M+H]^+$

(60) 1-(2-trifluoromethyl-4-cyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=500 $[M+H]^+$

(61) 1-(3,5-dicyano-benzyl)-3-methyl-7-(2-butyn-1-yl)-8-((R)-3-amino-piperidin-1-yl)-xanthine (BOC cleaving carried out with trifluoroacetic acid)

Mass spectrum ($ESI^+$): m/z=457 $[M+H]^+$

(62) 1-(3-nitro-4-cyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum ($ESI^+$): m/z=477 $[M+H]^+$

(63) 1-[(2-cyano-pyridin-3-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.50 (reversed phase ready-made TLC plate (E. Merck), acetonitrile/water/trifluoroacetic acid=50:50:1)

Mass spectrum ($ESI^+$): m/z=433 $[M+H]^+$

(64) 1-(2-cyano-4-methoxy-benzyl)-3-methyl-7-(2-butyn-1-yl)-8-((R)-3-amino-piperidin-1-yl)-xanthine (BOC cleaving carried out with trifluoroacetic acid)

$R_f$ value: 0.50 (reversed phase ready-made TLC plate (E. Merck), acetonitrile/water/trifluoroacetic acid=50:50:1)

Mass spectrum (ESI$^+$): m/z=462 [M+H]$^+$

(65) 1-(2-cyano-5-methoxy-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (reversed phase ready-made TLC plate (E. Merck), acetonitrile/water/trifluoroacetic acid=50:50:1)

Mass spectrum (ESI$^+$): m/z=462 [M+H]$^+$

(66) 1-(3-methoxy-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum (ESI$^+$): m/z=437 [M+H]$^+$

(67) 1-(3-trifluoromethyl-benzyl)-3-methyl-7-(2-butyn-1-yl)-8-((R)-3-amino-piperidin-1-yl)-xanthine (BOC cleaving carried out with trifluoroacetic acid)

$R_f$ value: 0.60 (silica gel, methylene chloride/methanol/conc. aqueous ammonia=90:10:0.1)

Mass spectrum (ESI$^+$): m/z=475 [M+H]$^+$

(68) 1-(3,4-dimethoxy-benzyl)-3-methyl-7-(2-butyn-1-yl)-8-((R)-3-amino-piperidin-1-yl)-xanthine (BOC cleaving carried out with trifluoroacetic acid)

$R_f$ value: 0.50 (silica gel, methylene chloride/methanol/conc. aqueous ammonia=90:10:0.1)

Mass spectrum (ESI$^+$): m/z=467 [M+H]$^+$

(69) 1-(3-chloro-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum (ESI$^+$): m/z=441, 443 [M+H]$^+$

(70) 1-(4-trifluoromethyl-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum (ESI$^+$): m/z=475 [M+H]$^+$

(71) 1-[([2,2']bipyridinyl-6-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:1)

Mass spectrum (ESI$^+$): m/z=485 [M+H]$^+$

(72) 1-(3,4-dimethoxy-6-fluoro-benzyl)-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)

Mass spectrum (ESI$^+$): m/z=485 [M+H]$^+$

(73) 1-[(6-fluoro-pyridin-2-yl)methyl]-3-methyl-7-(2-butyn-1-yl)-8-((R)-3-amino-piperidin-1-yl)-xanthine $R_f$ value: 0.41 (silica gel, methylene chloride/methanol/conc. aqueous ammonia=90:10:1)

Mass spectrum (ESI$^+$): m/z=426 [M+H]$^+$

(74) 1-[(5-cyano-6-methoxy-pyridin-2-yl)methyl]-3-methyl-7-(2-butyn-1-yl)-8-((R)-3-amino-piperidin-1-yl)-xanthine $R_f$ value: 0.40 (silica gel, methylene chloride/methanol/conc. aqueous ammonia=90:10:1)

Mass spectrum (ESI$^+$): m/z=463 [M+H]$^+$

(75) 1-(2,6-difluoro-benzyl)-3-methyl-7-(2-butyn-1-yl)-8-((R)-3-amino-piperidin-1-yl)-xanthine $R_f$ value: 0.41 (silica gel, methylene chloride/methanol/conc. aqueous ammonia=90:10:1)

Mass spectrum (ESI$^+$): m/z=443 [M+H]$^+$

(76) 1-(3-trifluoromethoxy-benzyl)-3-methyl-7-(2-butyn-1-yl)-8-((R)-3-amino-piperidin-1-yl)-xanthine $R_f$ value: 0.36 (silica gel, methylene chloride/methanol/conc. aqueous ammonia=90:10:1)

Mass spectrum (ESI$^+$): m/z=491 [M+H]$^+$

(77) 1-(4-trifluoromethoxy-benzyl)-3-methyl-7-(2-butyn-1-yl)-8-((R)-3-amino-piperidin-1-yl)-xanthine $R_f$ value: 0.38 (silica gel, methylene chloride/methanol/conc. aqueous ammonia=90:10:1)

Mass spectrum (ESI$^+$): m/z=491 [M+H]$^+$

(78) 1-[(2-cyano-pyridin-4-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.60 (reversed phase ready-made TLC plate (E. Merck), acetonitrile/water/trifluoroacetic acid=50:50:1)

Mass spectrum (ESI$^+$): m/z=433 [M+H]$^+$

(79) 1-[(5-cyano-pyridin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.60 (reversed phase ready-made TLC plate (E. Merck), acetonitrile/water/trifluoroacetic acid=50:50:1)

Mass spectrum (ESI$^+$): m/z=433 [M+H]$^+$

(80) 1-[(pyrimidin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.60 (reversed phase ready-made TLC plate (E. Merck), acetonitrile/water/trifluoroacetic acid=50:50:1)

Mass spectrum (ESI$^+$): m/z=409 [M+H]$^+$

(81) 1-[(4-methyl-pyrimidin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.65 (reversed phase ready-made TLC plate (E. Merck), acetonitrile/water/trifluoroacetic acid=50:50:1)

Mass spectrum (ESI$^+$): m/z=423 [M+H]$^+$

(82) 1-[(4,6-dimethyl-pyrimidin-2-yl)methyl]-3-methyl-7-(2-butyn-1-yl)-8-((R)-3-amino-piperidin-1-yl)-xanthine (BOC cleaving carried out with trifluoroacetic acid)

melting point: 202-204° C.

Mass spectrum (ESI$^+$): m/z=437 [M+H]$^+$

(83) 1-[(quinoxalin-6-yl)methyl]-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)

Mass spectrum (ESI$^+$): m/z=459 [M+H]$^+$

(84) 1-(3-fluoro-4-methoxy-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum (ESI$^+$): m/z=455 [M+H]$^+$

(85) 1-(3,4-difluoro-benzyl)-3-methyl-7-(2-butyn-1-yl)-8-((R)-3-amino-piperidin-1-yl)-xanthine (BOC cleaving carried out with trifluoroacetic acid)

$R_f$ value: 0.45 (silica gel, methylene chloride/methanol/conc. aqueous ammonia=90:10:0.1)

Mass spectrum (ESI$^+$): m/z=443 [M+H]$^+$

(86) 1-(2-fluoro-5-methoxy-benzyl)-3-methyl-7-(2-butyn-1-yl)-8-((R)-3-amino-piperidin-1-yl)-xanthine $R_f$ value: 0.39 (silica gel, methylene chloride/methanol/conc. aqueous ammonia=90:10:1)

Mass spectrum (ESI$^+$): m/z=455 [M+H]$^+$

(87) 1-(2-fluoro-3-methoxy-benzyl)-3-methyl-7-(2-butyn-1-yl)-8-((R)-3-amino-piperidin-1-yl)-xanthine $R_f$ value: 0.41 (silica gel, methylene chloride/methanol/conc. aqueous ammonia=90:10:1)

Mass spectrum (ESI$^+$): m/z=455 [M+H]$^+$

(88) 1-[(4-cyano-isoquinolin-3-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.40 (silica gel, methylene chloride/methanol/conc. aqueous ammonia=90:10:0.1)

Mass spectrum (ESI$^+$): m/z=483 [M+H]$^+$

(89) 1-(2-fluoro-4-methoxy-benzyl)-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:1)

Mass spectrum (ESI$^+$): m/z=455 [M+H]$^+$

(90) 1-[(furan-2-yl)methyl]-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=397 [M+H]$^+$

(91) 1-(3,4-dicyano-benzyl)-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum (ESI$^+$): m/z=457 [M+H]$^+$

(92) 1-[(furan-3-yl)methyl]-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=397 [M+H]$^+$

(93) 1-[(5-methyl-furan-2-yl)methyl]-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=411 [M+H]$^+$

(94) 1-[(5-bromo-furan-2-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum (ESI$^+$): m/z=475, 477 [M+H]$^+$

(95) 1-(4-cyano-2-fluoro-benzyl)-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=450 [M+H]$^+$

(96) 1-(2-cyano-5-fluoro-benzyl)-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=450 [M+H]$^+$

(97) 1-[(5-cyano-furan-2-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)

Mass spectrum (ESI$^+$): m/z=422 [M+H]$^+$

(98) 1-(2-cyano-6-fluoro-benzyl)-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=450 [M+H]$^+$

(99) 1-(4-cyano-3-fluoro-benzyl)-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=450 [M+H]$^+$ (100) 1-(2-cyano-3-methoxy-benzyl)-3-methyl-7-(2-butyn-1-yl)-8-((R)-3-amino-piperidin-1-yl)-xanthine $R_f$ value: 0.50 (silica gel, methylene chloride/methanol/conc. aqueous ammonia=90:10:0.1)

Mass spectrum (ESI$^+$): m/z=462 [M+H]$^+$ (101) 1-[(8-cyano-quinolin-7-yl)methyl]-3-methyl-7-(2-butyn-1-yl)-8-((R)-3-amino-piperidin-1-yl)-xanthine (BOC cleaving carried out with trifluoroacetic acid)

Mass spectrum (ESI$^+$): m/z=483 [M+H]$^+$ (102) 1-[(4-cyano-pyridin-3-yl)methyl]-3-methyl-7-(2-butyn-1-yl)-8-((R)-3-amino-piperidin-1-yl)-xanthine (BOC cleaving carried out with trifluoroacetic acid)

melting point: 166° C.

Mass spectrum (ESI$^+$): m/z=433 [M+H]$^+$ (103) 1-[(8-cyano-quinolin-2-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.50 (silica gel, methylene chloride/methanol/conc. aqueous ammonia=90:10:0.1)

Mass spectrum (ESI$^+$): m/z=483 [M+H]$^+$ (104) 1-[(1-methyl-1H-benzotriazol-5-yl)methyl]-3-methyl-7-(2-butyn-1-yl)-8-((R)-3-amino-piperidin-1-yl)-xanthine (BOC cleaving carried out with trifluoroacetic acid)

$R_f$ value: 0.60 (reversed phase ready-made TLC plate (E. Merck), acetonitrile/water/trifluoroacetic acid=50:50:1)

Mass spectrum (ESI$^+$): m/z=462 [M+H]$^+$ (105) 1-[(3-cyano-pyridin-4-yl)methyl]-3-methyl-7-(2-butyn-1-yl)-8-((R)-3-amino-piperidin-1-yl)-xanthine x trifluoroacetic acid (BOC cleaving carried out with trifluoroacetic acid)

$R_f$ value: 0.65 (reversed phase ready-made TLC plate (E. Merck), acetonitrile/water/trifluoroacetic acid=50:50:1)

Mass spectrum (ESI$^+$): m/z=433 [M+H]$^+$ (106) 1-[(3-cyano-pyridin-2-yl)methyl]-3-methyl-7-(2-butyn-1-yl)-8-((S)-3-amino-piperidin-1-yl)-xanthine (BOC cleaving carried out with trifluoroacetic acid)

$R_f$ value: 0.60 (reversed phase ready-made TLC plate (E. Merck), acetonitrile/water/trifluoroacetic acid=50:50:1)

Mass spectrum (ESI$^+$): m/z=433 [M+H]$^+$ (107) 1-[(4-cyano-benzo[1,3]dioxol-5-yl)methyl]-3-methyl-7-(2-butyn-1-yl)-8-((R)-3-amino-piperidin-1-yl)-xanthine $R_f$ value: 0.45 (silica gel, methylene chloride/methanol/conc. aqueous ammonia=90:10:0.1)

Mass spectrum (ESI$^+$): m/z=476 [M+H]$^+$

The following compounds may also be obtained analogously to the foregoing Examples and other methods known from the literature:

(1) 1-(2-cyano-4-fluoro-benzyl)-3-methyl-7-(2-butyn-1-yl)-8-((R)-3-amino-piperidin-1-yl)-xanthine (2) 1-(2-cyano-5-fluoro-benzyl)-3-methyl-7-(2-butyn-1-yl)-8-((R)-3-amino-piperidin-1-yl)-xanthine (3) 1-(2-cyano-6-fluoro-benzyl)-3-methyl-7-(2-butyn-1-yl)-8-((R)-3-amino-piperidin-1-yl)-xanthine (4) 1-(3-cyano-4-fluoro-benzyl)-3-methyl-7-(2-butyn-1-yl)-8-((R)-3-amino-piperidin-1-yl)-xanthine (5) 1-(3,5-dicyano-benzyl)-3-methyl-7-(2-butyn-1-yl)-8-((R)-3-amino-piperidin-1-yl)-xanthine (6) 1-(3,4-dicyano-benzyl)-3-methyl-7-(2-butyn-1-yl)-8-((R)-3-amino-piperidin-1-yl)-xanthine (7) 1-(3-nitro-4-cyano-benzyl)-3-methyl-7-(2-butyn-1-yl)-8-((R)-3-amino-piperidin-1-yl)-xanthine (8) 1-(2-chloro-4-cyano-benzyl)-3-methyl-7-(2-butyn-1-yl)-8-((R)-3-amino-piperidin-1-yl)-xanthine (9) 1-(2-fluoro-4-cyano-benzyl)-3-methyl-7-(2-butyn-1-yl)-8-((R)-3-amino-piperidin-1-yl)-xanthine

(10) 1-(2-trifluoromethyl-4-cyano-benzyl)-3-methyl-7-(2-butyn-1-yl)-8-((R)-3-amino-piperidin-1-yl)-xanthine

(11) 1-[(5-cyano-pyridin-2-yl)methyl]-3-methyl-7-(2-butyn-1-yl)-8-((R)-3-amino-piperidin-1-yl)-xanthine

(12) 1-[(4-cyano-pyridin-2-yl)methyl]-3-methyl-7-(2-butyn-1-yl)-8-((R)-3-amino-piperidin-1-yl)-xanthine
(13) 1-[(4-cyano-pyridin-3-yl)methyl]-3-methyl-7-(2-butyn-1-yl)-8-((R)-3-amino-piperidin-1-yl)-xanthine
(14) 1-[(3-cyano-pyridin-4-yl)methyl]-3-methyl-7-(2-butyn-1-yl)-8-((R)-3-amino-piperidin-1-yl)-xanthine
(15) 1-[(2-cyano-pyridin-3-yl)methyl]-3-methyl-7-(2-butyn-1-yl)-8-((R)-3-amino-piperidin-1-yl)-xanthine
(16) 1-[(2-cyano-pyridin-4-yl)methyl]-3-methyl-7-(2-butyn-1-yl)-8-((R)-3-amino-piperidin-1-yl)-xanthine
(17) 1-[(5-cyano-pyridin-3-yl)methyl]-3-methyl-7-(2-butyn-1-yl)-8-((R)-3-amino-piperidin-1-yl)-xanthine
(18) 1-[(6-cyano-pyridin-3-yl)methyl]-3-methyl-7-(2-butyn-1-yl)-8-((R)-3-amino-piperidin-1-yl)-xanthine
(19) 1-(2-cyano-4-methoxy-benzyl)-3-methyl-7-(2-butyn-1-yl)-8-((R)-3-amino-piperidin-1-yl)-xanthine
(20) 1-(2-cyano-5-methoxy-benzyl)-3-methyl-7-(2-butyn-1-yl)-8-((R)-3-amino-piperidin-1-yl)-xanthine
(21) 1-[([2,2']bipyridinyl-6-yl)methyl]-3-methyl-7-(2-butyn-1-yl)-8-((R)-3-amino-piperidin-1-yl)-xanthine
(22) 1-[(5-methoxy-pyridin-2-yl)methyl]-3-methyl-7-(2-butyn-1-yl)-8-((R)-3-amino-piperidin-1-yl)-xanthine
(23) 1-[(6-fluoro-pyridin-2-yl)methyl]-3-methyl-7-(2-butyn-1-yl)-8-((R)-3-amino-piperidin-1-yl)-xanthine
(24) 1-[(5-cyano-6-methoxy-pyridin-2-yl)methyl]-3-methyl-7-(2-butyn-1-yl)-8-((R)-3-amino-piperidin-1-yl)-xanthine
(25) 1-(2-methoxy-benzyl)-3-methyl-7-(2-butyn-1-yl)-8-((R)-3-amino-piperidin-1-yl)-xanthine
(26) 1-(3-methoxy-benzyl)-3-methyl-7-(2-butyn-1-yl)-8-((R)-3-amino-piperidin-1-yl)-xanthine
(27) 1-(3-chloro-benzyl)-3-methyl-7-(2-butyn-1-yl)-8-((R)-3-amino-piperidin-1-yl)-xanthine
(28) 1-(4-trifluoromethyl-benzyl)-3-methyl-7-(2-butyn-1-yl)-8-((R)-3-amino-piperidin-1-yl)-xanthine
(29) 1-(3-trifluoromethyl-benzyl)-3-methyl-7-(2-butyn-1-yl)-8-((R)-3-amino-piperidin-1-yl)-xanthine
(30) 1-(2-trifluoromethyl-benzyl)-3-methyl-7-(2-butyn-1-yl)-8-((R)-3-amino-piperidin-1-yl)-xanthine
(31) 1-(3,4-dimethoxy-benzyl)-3-methyl-7-(2-butyn-1-yl)-8-((R)-3-amino-piperidin-1-yl)-xanthine
(32) 1-(3,4-dimethoxy-6-fluoro-benzyl)-3-methyl-7-(2-butyn-1-yl)-8-((R)-3-amino-piperidin-1-yl)-xanthine
(33) 1-[(benzo[1,3]dioxol-5-yl)methyl]-3-methyl-7-(2-butyn-1-yl)-8-((R)-3-amino-piperidin-1-yl)-xanthine

EXAMPLE 2

Coated Tablets Containing 75 mg of Active Substance 1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| | |
|---|---|
| Weight of core: | 230 mg |
| Die: | 9 mm, convex |

The tablet cores thus produced are coated with a film consisting essentially of hydroxypropylmethylcellulose. The finished film-coated tablets are polished with beeswax.

Weight of coated tablet: 245 mg.

EXAMPLE 3

Tablets Containing 100 mg of Active Substance

Composition:

1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

EXAMPLE 4

Tablets Containing 150 mg of Active Substance

Composition:

1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| Die: | 10 mm, flat |

EXAMPLE 5

Hard Gelatine Capsules Containing 150 mg of Active Substance 1 capsule contains:

| | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| | |
|---|---|
| Capsule filling: | approx. 320 mg |
| Capsule shell: | size 1 hard gelatine capsule. |

EXAMPLE 6

Suppositories Containing 150 mg of Active Substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 7

Suspension Containing 50 mg of Active Substance 100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavoring have been added and dissolved, the suspension is evacuated with stirring to eliminate air.

5 ml of suspension contains 50 mg of active substance.

EXAMPLE 8

Ampoules Containing 10 mg Active Substance

Composition:

| | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 9

Ampoules Containing 50 mg of Active Substance

Composition:

| | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:

1. A compound of the formula (I):

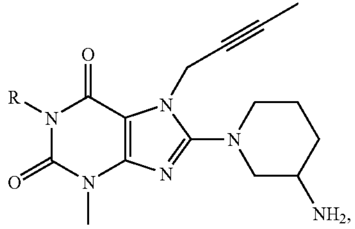

wherein

R denotes:

a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl or 4-chlorobenzyl group, a 2-trifluoromethyl-benzyl, 3-trifluoromethyl-benzyl or 4-trifluoromethyl-benzyl group, a 3-trifluoromethoxy-benzyl or 4-trifluoromethoxy-benzyl group, a 2-cyanobenzyl, 3-cyanobenzyl or 4-cyanobenzyl group, a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl or 2-cyano-4-bromobenzyl group, a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl or 3,4-dimethoxy-6-fluoro-benzyl group, a (furan-2-yl)methyl, (furan-3-yl)methyl, (5-bromo-furan-2-yl)methyl, (5-methyl-furan-2-yl)methyl, (5-cyano-furan-2-yl)methyl or (5-methoxycarbonyl-furan-2-yl)methyl group, a (pyridin-2-yl)methyl, (6-fluoro-pyridin-2-yl)methyl or (5-methoxy-pyridin-2-yl)methyl group, a (3-cyanopyridin-2-yl)methyl, (6-cyanopyridin-2-yl)methyl, (5-cyano-pyridin-2-yl)methyl, (4-cyano-pyridin-2-yl) methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl or (5-cyano-6-methoxy-pyridin-2-yl) methyl group, a (6-phenyl-pyridin-2-yl)methyl or a ([2,2']bipyridinyl-6-yl)methyl group, a (pyrimidin-2-yl)methyl, (4-methyl-pyrimidin-2-yl)methyl or (4,6-dimethyl-pyrimidin-2-yl)methyl group, or a (2-phenyl-pyrimidin-4-yl)methyl or (4-phenyl-pyrimidin-2-yl)methyl group, or diastereomer thereof, or a mixture thereof, or a salt thereof.

2. A compound of the formula (Ia):

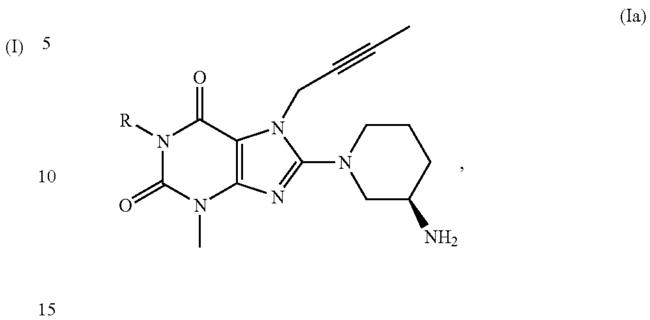

wherein R denotes:

a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl or 4-chlorobenzyl group, a 2-trifluoromethyl-benzyl, 3-trifluoromethyl-benzyl or 4-trifluoromethyl-benzyl group, a 3-trifluoromethoxy-benzyl or 4-trifluoromethoxy-benzyl group, a 2-cyanobenzyl, 3-cyanobenzyl or 4-cyanobenzyl group, a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl or 2-cyano-4-bromobenzyl group, a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl or 3,4-dimethoxy-6-fluoro-benzyl group, a (furan-2-yl)methyl, (furan-3-yl)methyl, (5-bromo-furan-2-yl)methyl, (5-methyl-furan-2-yl)methyl, (5-cyano-furan-2-yl)methyl or (5-methoxycarbonyl-furan-2-yl)methyl group, a (pyridin-2-yl)methyl, (6-fluoro-pyridin-2-yl)methyl or (5-methoxy-pyridin-2-yl)methyl group, a (3-cyanopyridin-2-yl)methyl, (6-cyanopyridin-2-yl)methyl, (5-cyano-pyridin-2-yl)methyl, (4-cyano-pyridin-2-yl) methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl or (5-cyano-6-methoxy-pyridin-2-yl) methyl group, a (6-phenyl-pyridin-2-yl)methyl or a ([2,2']bipyridinyl-6-yl)methyl group, a (pyrimidin-2-yl)methyl, (4-methyl-pyrimidin-2-yl)methyl or (4,6-dimethyl-pyrimidin-2-yl)methyl group, or a (2-phenyl-pyrimidin-4-yl)methyl or (4-phenyl-pyrimidin-2-yl)methyl group, or a tautomer or salt thereof.

3. A compound of the formula (Ib):

(Ib)

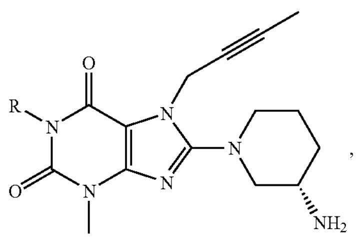

wherein R denotes:

a benzyl, 2-fluorobenzyl, 3-fluorobenzyl, 4-fluorobenzyl, 2,6-difluoro-benzyl, 3,4-difluoro-benzyl, 2-chlorobenzyl, 3-chlorobenzyl or 4-chlorobenzyl group, a 2-trifluoromethyl-benzyl, 3-trifluoromethyl-benzyl or 4-trifluoromethyl-benzyl group, a 3-trifluoromethoxy-benzyl or 4-trifluoromethoxy-benzyl group, a 2-cyanobenzyl, 3-cyanobenzyl or 4-cyanobenzyl group, a 2,6-dicyanobenzyl, 3,4-dicyanobenzyl, 3,5-dicyanobenzyl, 2-trifluoromethyl-4-cyano-benzyl, 3-nitro-4-cyano-benzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 3-cyano-4-fluoro-benzyl, 4-cyano-3-fluoro-benzyl, 2-fluoro-4-cyano-benzyl, 2-cyano-3-chlorobenzyl, 2-chloro-4-cyano-benzyl or 2-cyano-4-bromobenzyl group, a 2-methoxy-benzyl, 3-methoxy-benzyl, 4-methoxy-benzyl, 2-fluoro-3-methoxy-benzyl, 2-fluoro-4-methoxy-benzyl, 2-fluoro-5-methoxy-benzyl, 3-fluoro-4-methoxy-benzyl, 3,4-dimethoxy-benzyl, 3,5-dimethoxybenzyl or 3,4-dimethoxy-6-fluoro-benzyl group, a (furan-2-yl)methyl, (furan-3-yl)methyl, (5-bromo-furan-2-yl)methyl, (5-methyl-furan-2-yl)methyl, (5-cyano-furan-2-yl)methyl or (5-methoxycarbonyl-furan-2-yl)methyl group, a (pyridin-2-yl)methyl, (6-fluoro-pyridin-2-yl)methyl or (5-methoxy-pyridin-2-yl)methyl group, a (3-cyanopyridin-2-yl)methyl, (6-cyanopyridin-2-yl)methyl, (5-cyano-pyridin-2-yl)methyl, (4-cyano-pyridin-2-yl) methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl or (5-cyano-6-methoxy-pyridin-2-yl) methyl group, a (6-phenyl-pyridin-2-yl)methyl or a ([2,2']bipyridinyl-6-yl)methyl group, a (pyrimidin-2-yl)methyl, (4-methyl-pyrimidin-2-yl)methyl or (4,6-dimethyl-pyrimidin-2-yl)methyl group, or a (2-phenyl-pyrimidin-4-yl)methyl or (4-phenyl-pyrimidin-2-yl)methyl group, or a tautomer or salt thereof.

4. A physiologically acceptable salt of the compound according to claim 1, with inorganic or organic acids.

5. A physiologically acceptable salt of the compound according to claim 2, with inorganic or organic acids.

6. A physiologically acceptable salt of the compound according to claim 3, with inorganic or organic acids.

7. A pharmaceutical composition comprising a compound according to claim 1, with one or more inert carriers or diluents.

8. A pharmaceutical composition comprising a compound according to claim 2, with one or more inert carriers or diluents.

9. A pharmaceutical composition comprising a compound according to claim 3, with one or more inert carriers or diluents.

10. A method of treating type II diabetes mellitus or obesity, comprising administering to a patient a pharmaceutically effective amount of a compound according to claim 1.

11. A method of treating type II diabetes mellitus or obesity, comprising administering to a patient a pharmaceutically effective amount of a compound according to claim 2.

12. A method of treating type II diabetes mellitus or obesity, comprising administering to a patient a pharmaceutically effective amount of a compound according to claim 3.

13. A compound of the formula (Ia) or a physiologically acceptable salt thereof with an inorganic or organic acid (Ia)

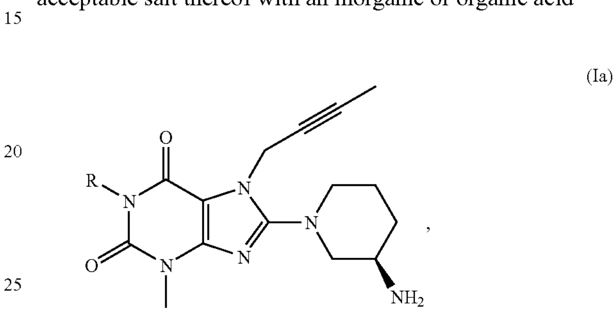

wherein R denotes a (3-cyanopyridin-2-yl)methyl group.

14. A pharmaceutical composition comprising one or more inert carriers or diluents and a compound of the formula (Ia) or a physiologically acceptable salt thereof with an inorganic or organic acid (Ia)

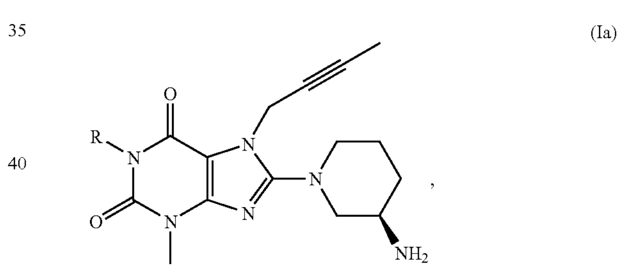

wherein R denotes a (3-cyanopyridin-2-yl)methyl group.

15. A method of treating type II diabetes mellitus or obesity, comprising the step of administering to a patient a pharmaceutically effective amount of a compound of the formula (Ia) or a physiologically acceptable salt thereof with an inorganic or organic acid (Ia)

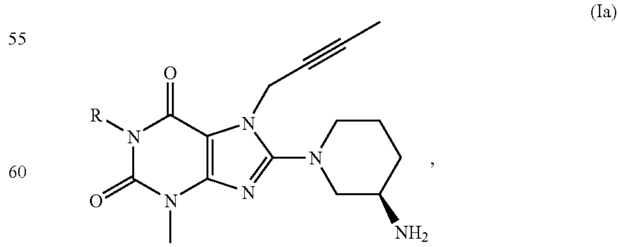

wherein R denotes a (3-cyanopyridin-2-yl)methyl group.

16. A method of treating type II diabetes mellitus comprising the step of administering to a patient a pharmaceutically effective amount of a compound of the formula (Ia) or a physiologically acceptable salt thereof with an inorganic or organic acid (Ia)

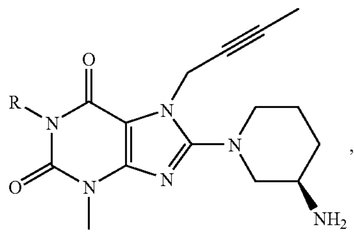

wherein R denotes a (3-cyanopyridin-2-yl)methyl group.

17. The compound 1-[(3-cyano-pyridin-2-yl)methyl]-3-methyl-7-(2-butyn-1-yl)-8-((R)-3-amino-piperidin-1-yl)-xanthine in a physiologically acceptable salt form with an inorganic or organic acid.

18. A pharmaceutical composition comprising one or more inert carriers or diluents and 1-[(3-cyano-pyridin-2-yl)methyl]-3-methyl-7-(2-butyn-1-yl)-8-((R)-3-amino-piperidin-1-yl)-xanthine in a physiologically acceptable salt form with an inorganic or organic acid.

19. A method of treating type II diabetes mellitus or obesity, comprising the step of administering to a patient a pharmaceutically effective amount of 1-[(3-cyano-pyridin-2-yl)methyl]-3-methyl-7-(2-butyn-1-yl)-8-((R)-3-amino-piperidin-1-yl)-xanthine in a physiologically acceptable salt form with an inorganic or organic acid.

20. A method of treating type II diabetes mellitus comprising the step of administering to a patient a pharmaceutically effective amount of 1-[(3-cyano-pyridin-2-yl)methyl]-3-methyl-7-(2-butyn-1-yl)-8-((R)-3-amino-piperidin-1-yl)-xanthine in a physiologically acceptable salt form with an inorganic or organic acid.

* * * * *